(12) United States Patent
Dempsey et al.

(10) Patent No.: US 11,033,758 B2
(45) Date of Patent: Jun. 15, 2021

(54) RADIOTHERAPY SYSTEMS, METHODS AND SOFTWARE

(71) Applicant: ViewRay Technologies, Inc., Oakwood Village, OH (US)

(72) Inventors: James F. Dempsey, Atherton, CA (US); Iwan Kawrykow, Sofia (BG)

(73) Assignee: VIEWRAY TECHNOLOGIES, INC., Oakwood Village, OH (US)

( * ) Notice: Subject to any disclaimer, the term of this patent is extended or adjusted under 35 U.S.C. 154(b) by 0 days.

(21) Appl. No.: 16/204,838

(22) Filed: Nov. 29, 2018

(65) Prior Publication Data
US 2019/0168028 A1    Jun. 6, 2019

Related U.S. Application Data

(60) Provisional application No. 62/595,478, filed on Dec. 6, 2017.

(51) Int. Cl.
*A61N 5/00* (2006.01)
*A61N 5/10* (2006.01)

(52) U.S. Cl.
CPC ......... *A61N 5/1071* (2013.01); *A61N 5/1039* (2013.01); *A61N 5/1067* (2013.01);
(Continued)

(58) Field of Classification Search
CPC .. A61N 5/1071; A61N 5/1039; A61N 5/1067; A61N 5/1077; A61N 5/1081;
(Continued)

(56) References Cited

U.S. PATENT DOCUMENTS 3,428,307 A    2/1969 Hunter
3,569,823 A    3/1971 Golay
(Continued)

FOREIGN PATENT DOCUMENTS

CN    1394550 A    2/2003
CN    1612713 A    5/2005
(Continued)

OTHER PUBLICATIONS

PCT App. No. PCT/2018/063108; International Search Report and Written Opinion dated May 10, 2019; 14 pages.
(Continued)

*Primary Examiner* — Dani Fox
(74) *Attorney, Agent, or Firm* — Pillsbury Winthrop Shaw Pittman LLP

(57) ABSTRACT

A photon therapy delivery system can deliver radiation therapy to a patient via a photon beam. The system can utilize a controller configured to facilitate delivery of radiation therapy via a photon beam and also a particle beam. This can include receiving radiation therapy beam information for radiation therapy treatment of a patient utilizing the particle beam and photon beam. Also, patient magnetic resonance imaging (MRI) data can be received during the radiation therapy treatment. Utilizing the patient MRI data, real-time calculations of a location of dose deposition for the particle beam and for the photon beam can be determined taking into account interaction properties of soft tissues through which the particle beam passes.

16 Claims, 9 Drawing Sheets

(52) U.S. Cl.
CPC ......... *A61N 5/1077* (2013.01); *A61N 5/1081* (2013.01); *A61N 2005/109* (2013.01); *A61N 2005/1055* (2013.01); *A61N 2005/1072* (2013.01); *A61N 2005/1074* (2013.01); *A61N 2005/1087* (2013.01); *A61N 2005/1094* (2013.01)

(58) Field of Classification Search
CPC .... A61N 2005/1055; A61N 2005/1072; A61N 2005/1074; A61N 2005/1087; A61N 2005/109; A61N 2005/1094
USPC .......................................................... 378/65
See application file for complete search history.

(56) References Cited

U.S. PATENT DOCUMENTS

| | | |
|---|---|---|
| 3,735,306 A | 5/1973 | Kabler |
| 4,019,059 A | 4/1977 | Brundin |
| 4,233,662 A | 11/1980 | LeMay |
| 4,481,657 A | 11/1984 | Larsson |
| 4,589,126 A | 5/1986 | Augustsson |
| 4,642,569 A | 2/1987 | Hayes |
| 4,652,826 A | 3/1987 | Yamamoto |
| 4,694,837 A | 9/1987 | Blakeley |
| 4,740,753 A | 4/1988 | Glover |
| 4,771,785 A | 9/1988 | Duer |
| 4,851,778 A | 7/1989 | Kaufman |
| 4,987,309 A | 1/1991 | Klasen |
| 5,006,804 A | 4/1991 | Dorri |
| 5,027,818 A | 7/1991 | Bova |
| 5,039,867 A | 8/1991 | Nishihara |
| 5,094,837 A | 3/1992 | Bis |
| 5,117,829 A | 6/1992 | Miller |
| 5,216,255 A | 6/1993 | Weidlich |
| 5,280,428 A | 1/1994 | Wu |
| 5,295,488 A | 3/1994 | Lloyd |
| 5,317,616 A | 5/1994 | Swerdloff |
| 5,327,884 A | 7/1994 | Hardy |
| 5,328,681 A | 7/1994 | Kito |
| 5,331,552 A | 7/1994 | Lloyd |
| 5,332,908 A | 7/1994 | Weidlich |
| 5,351,280 A | 9/1994 | Swerdloff |
| 5,361,763 A | 11/1994 | Kao |
| 5,365,927 A | 11/1994 | Roemer |
| 5,373,239 A | 12/1994 | Marek |
| 5,373,844 A | 12/1994 | Smith |
| 5,377,678 A | 1/1995 | Dumoulin |
| 5,378,989 A | 1/1995 | Barber |
| 5,391,139 A | 2/1995 | Edmundson |
| 5,412,823 A | 5/1995 | Sitta |
| 5,442,675 A | 8/1995 | Swerdloff |
| 5,443,068 A | 8/1995 | Cline |
| 5,458,125 A | 10/1995 | Schweikard |
| 5,511,549 A | 4/1996 | Legg |
| 5,513,238 A | 4/1996 | Leber |
| 5,530,352 A | 6/1996 | Kolem |
| 5,537,452 A | 7/1996 | Shepherd |
| 5,538,494 A | 7/1996 | Matsuda |
| 5,547,454 A | 8/1996 | Horn |
| 5,555,283 A | 9/1996 | Shiu |
| 5,585,724 A | 12/1996 | Morich |
| 5,592,091 A | 1/1997 | Manabe |
| 5,596,619 A | 1/1997 | Carol |
| 5,602,892 A | 2/1997 | Llacer |
| 5,602,982 A | 2/1997 | Llacer |
| 5,647,361 A | 7/1997 | Damadian |
| 5,659,281 A | 8/1997 | Pissanetzky |
| 5,675,305 A | 10/1997 | Demeester |
| 5,722,411 A | 3/1998 | Suzuki |
| 5,724,400 A | 3/1998 | Swerdloff |
| 5,734,384 A | 3/1998 | Yanof |
| 5,740,225 A | 4/1998 | Nabatame |
| 5,748,700 A | 5/1998 | Shepherd |
| 5,751,781 A | 5/1998 | Brown |
| 5,757,881 A | 5/1998 | Hughes |
| 5,760,582 A | 6/1998 | Morrone |
| 5,790,996 A | 8/1998 | Narfstrom |
| 5,802,136 A | 9/1998 | Carol |
| 5,815,547 A | 9/1998 | Shepherd |
| 5,851,182 A | 12/1998 | Sahadevan |
| 5,894,503 A | 4/1999 | Shepherd |
| 5,952,830 A | 9/1999 | Petropoulos |
| 5,993,373 A | 11/1999 | Nonaka |
| 6,005,916 A | 12/1999 | Johnson |
| 6,038,283 A | 3/2000 | Carol |
| 6,052,430 A | 4/2000 | Siochi |
| 6,094,760 A | 8/2000 | Nonaka |
| 6,104,779 A | 8/2000 | Shepherd |
| 6,112,112 A | 8/2000 | Gilhuijs |
| 6,125,335 A | 9/2000 | Simon |
| 6,144,875 A | 11/2000 | Schweikard |
| 6,157,278 A | 12/2000 | Katznelson |
| 6,175,761 B1 | 1/2001 | Frandsen |
| 6,198,957 B1 | 3/2001 | Green |
| 6,207,952 B1 | 3/2001 | Kan |
| 6,223,067 B1 | 4/2001 | Vilsmeier |
| 6,240,162 B1 | 5/2001 | Hernandez-Guerra |
| 6,260,005 B1 | 7/2001 | Yang |
| 6,273,858 B1 | 8/2001 | Fox |
| 6,278,891 B1 | 8/2001 | Reiderman |
| 6,311,389 B1 | 11/2001 | Uosaki |
| 6,314,159 B1 | 11/2001 | Siochi |
| 6,330,300 B1 | 12/2001 | Siochi |
| 6,349,129 B1 | 2/2002 | Siochi |
| 6,366,798 B2 | 4/2002 | Green |
| 6,373,250 B1 | 4/2002 | Tsoref |
| 6,381,486 B1 | 4/2002 | Mistretta |
| 6,385,286 B1 | 5/2002 | Fitchard |
| 6,385,477 B1 | 5/2002 | Werner |
| 6,393,096 B1 | 5/2002 | Carol |
| 6,405,072 B1 | 6/2002 | Cosman |
| 6,411,675 B1 | 6/2002 | Llacer |
| 6,414,487 B1 | 7/2002 | Anand |
| 6,422,748 B1 | 7/2002 | Shepherd |
| 6,424,856 B1 | 7/2002 | Vilsmeier |
| 6,459,769 B1 | 10/2002 | Cosman |
| 6,466,813 B1 | 10/2002 | Shukla |
| 6,487,435 B2 | 11/2002 | Mistretta |
| 6,504,899 B2 | 1/2003 | Pugachev |
| 6,509,735 B2 | 1/2003 | Mueller |
| 6,512,813 B1 | 1/2003 | Krispel |
| 6,512,942 B1 | 1/2003 | Burdette |
| 6,516,046 B1 | 2/2003 | Frohlich |
| 6,526,123 B2 | 2/2003 | Ein-Gal |
| 6,527,443 B1 | 3/2003 | Vilsmeier |
| 6,542,767 B1 | 4/2003 | McNichols |
| 6,546,073 B1 | 4/2003 | Lee |
| 6,560,311 B1 | 5/2003 | Shepard |
| 6,564,084 B2 | 5/2003 | Allred |
| 6,570,475 B1 | 5/2003 | Lvovsky |
| 6,584,174 B2 | 6/2003 | Schubert |
| 6,591,127 B1 | 7/2003 | McKinnon |
| 6,594,516 B1 | 7/2003 | Steckner |
| 6,600,810 B1 | 7/2003 | Hughes |
| 6,609,022 B2 | 8/2003 | Vilsmeier |
| 6,611,700 B1 | 8/2003 | Vilsmeier |
| 6,618,467 B1 | 9/2003 | Ruchala |
| 6,636,645 B1 | 10/2003 | Yu |
| 6,657,391 B2 | 12/2003 | Ding |
| 6,661,870 B2 | 12/2003 | Kapatoes |
| 6,708,054 B2 | 3/2004 | Shukla |
| 6,719,683 B2 | 4/2004 | Frohlich |
| 6,724,922 B1 | 4/2004 | Vilsmeier |
| 6,728,336 B2 | 4/2004 | Bortfeld |
| 6,731,970 B2 | 5/2004 | Schlossbauer |
| 6,735,277 B2 | 5/2004 | McNutt |
| 6,757,355 B1 | 6/2004 | Siochi |
| 6,772,002 B2 | 8/2004 | Schmidt |
| 6,778,850 B1 | 8/2004 | Adler |
| 6,788,060 B1 | 9/2004 | Feenan |
| 6,792,074 B2 | 9/2004 | Erbel |
| 6,806,712 B2 | 10/2004 | Akgun |
| 6,849,129 B2 | 2/2005 | Bilz et al. |

(56) References Cited

U.S. PATENT DOCUMENTS

| | | |
|---|---|---|
| 6,853,704 B2 | 2/2005 | Collins |
| 6,859,660 B2 | 2/2005 | Vilsmeier |
| 6,862,469 B2 | 3/2005 | Bucholz |
| 6,865,253 B2 | 3/2005 | Blumhofer |
| 6,865,411 B2 | 3/2005 | Erbel |
| 6,879,714 B2 | 4/2005 | Hutter |
| 6,885,886 B2 | 4/2005 | Bauch |
| 6,891,375 B2 | 5/2005 | Goto |
| 6,891,924 B1 | 5/2005 | Yoda |
| 6,898,456 B2 | 5/2005 | Erbel |
| 6,915,005 B1 | 7/2005 | Ruchala |
| 6,937,696 B1 | 8/2005 | Mostafavi |
| 6,940,281 B2 | 9/2005 | Feenan |
| 6,947,582 B1 | 9/2005 | Vilsmeier |
| 6,965,847 B2 | 11/2005 | Wessol |
| 6,980,679 B2 | 12/2005 | Jeung |
| 6,999,555 B2 | 2/2006 | Morf |
| 7,012,385 B1 | 3/2006 | Kulish |
| 7,046,762 B2 | 5/2006 | Lee |
| 7,046,765 B2 | 5/2006 | Wong |
| 7,046,831 B2 | 5/2006 | Ruchala |
| 7,050,845 B2 | 5/2006 | Vilsmeier |
| 7,092,573 B2 | 8/2006 | Luo |
| 7,095,823 B2 | 8/2006 | Topolnjak |
| 7,096,055 B1 | 8/2006 | Schweikard |
| 7,123,758 B2 | 10/2006 | Jeung |
| 7,130,372 B2 | 10/2006 | Kusch |
| 7,154,991 B2 | 12/2006 | Earnst |
| 7,162,005 B2 | 1/2007 | Bjorkholm |
| 7,166,852 B2 | 1/2007 | Saracen |
| 7,171,257 B2 | 1/2007 | Thomson |
| 7,180,366 B2 | 2/2007 | Roos |
| 7,191,100 B2 | 3/2007 | Mostafavi |
| 7,202,663 B2 | 4/2007 | Huang |
| 7,204,640 B2 | 4/2007 | Fu |
| 7,221,733 B1 | 5/2007 | Takai |
| 7,227,925 B1 | 6/2007 | Mansfield |
| 7,230,429 B1 | 6/2007 | Huang |
| 7,231,075 B2 | 6/2007 | Raghavan |
| 7,231,076 B2 | 6/2007 | Fu |
| 7,260,426 B2 | 8/2007 | Schweikard |
| 7,265,545 B2 | 9/2007 | Krueger |
| 7,266,175 B1 | 9/2007 | Romesberg |
| 7,266,176 B2 | 9/2007 | Allison |
| 7,289,599 B2 | 10/2007 | Seppi |
| 7,298,819 B2 | 11/2007 | Dooley |
| 7,302,038 B2 | 11/2007 | Mackie |
| 7,315,636 B2 | 1/2008 | Kuduvalli |
| 7,317,782 B2 | 1/2008 | Bjorkholm |
| 7,318,805 B2 | 1/2008 | Schweikard |
| 7,324,626 B2 | 1/2008 | Vilsmeier |
| 7,327,865 B2 | 2/2008 | Fu |
| 7,366,278 B2 | 4/2008 | Fu |
| 7,394,081 B2 | 7/2008 | Okazaki |
| 7,403,638 B2 | 7/2008 | Jeung |
| 7,412,029 B2 | 8/2008 | Myles |
| 7,415,095 B2 | 8/2008 | Wofford |
| 7,423,273 B2 | 9/2008 | Clayton |
| 7,426,318 B2 | 9/2008 | Fu |
| 7,444,178 B2 | 10/2008 | Goldbach |
| 7,453,264 B2 | 11/2008 | Trequattrini |
| 7,463,823 B2 | 12/2008 | Birkenbach |
| 7,471,813 B2 | 12/2008 | Ulmer |
| 7,477,776 B2 | 1/2009 | Lachner |
| 7,480,399 B2 | 1/2009 | Fu |
| 7,489,131 B2 | 2/2009 | Lvovsky |
| 7,505,037 B2 | 3/2009 | Wang |
| 7,505,617 B2 | 3/2009 | Fu |
| 7,522,779 B2 | 4/2009 | Fu |
| 7,532,705 B2 | 5/2009 | Yin |
| 7,535,229 B2 | 5/2009 | Schlueter |
| 7,542,622 B1 | 6/2009 | Angelini |
| 7,558,617 B2 | 7/2009 | Vilsmeier |
| 7,570,987 B2 | 8/2009 | Raabe |
| 7,577,474 B2 | 8/2009 | Vilsmeier |
| 7,589,326 B2 | 9/2009 | Mollov |
| 7,634,122 B2 | 12/2009 | Bertram |
| 7,636,417 B2 | 12/2009 | Bjorkholm |
| 7,638,752 B2 | 12/2009 | Partain |
| 7,657,304 B2 | 2/2010 | Mansfield |
| 7,659,718 B1 | 2/2010 | Lustig |
| 7,688,998 B2 | 3/2010 | Tuma |
| 7,728,311 B2 | 6/2010 | Gall |
| 7,741,624 B1 | 6/2010 | Sahadevan |
| 7,785,358 B2 | 8/2010 | Lach |
| 7,791,338 B2 | 9/2010 | Kim |
| 7,840,045 B2 | 11/2010 | Guo |
| 7,901,357 B2 | 3/2011 | Boctor |
| 7,902,530 B1 | 3/2011 | Sahadevan |
| 7,907,987 B2 | 3/2011 | Dempsey |
| 7,957,507 B2 | 6/2011 | Cadman |
| 8,139,714 B1 | 3/2012 | Sahadevan |
| 8,155,417 B2 | 4/2012 | Piron |
| 8,173,983 B1 * | 5/2012 | Sahadevan ........... A61N 5/1084 250/494.1 |
| 8,190,233 B2 | 5/2012 | Dempsey |
| 8,214,010 B2 | 7/2012 | Courtney |
| 8,310,233 B2 | 11/2012 | Trzasko |
| 8,331,531 B2 | 12/2012 | Fahrig |
| 8,334,697 B2 | 12/2012 | Overweg |
| 8,378,677 B2 | 2/2013 | Morich |
| 8,460,195 B2 | 6/2013 | Courtney |
| 8,570,042 B2 | 10/2013 | Pines |
| 8,637,841 B2 | 1/2014 | Prince |
| 8,803,524 B2 | 8/2014 | Dempsey |
| 8,812,077 B2 | 8/2014 | Dempsey |
| 8,836,332 B2 | 9/2014 | Shvartsman |
| 8,896,308 B2 | 11/2014 | Shvartsman |
| 8,981,779 B2 | 3/2015 | Shvartsman |
| 8,983,573 B2 | 3/2015 | Carlone |
| 9,082,520 B2 | 7/2015 | Prince |
| 9,114,253 B2 | 8/2015 | Dempsey |
| 9,289,626 B2 | 3/2016 | Kawrakow |
| 9,421,398 B2 | 8/2016 | Shvartsman |
| 9,423,477 B2 | 8/2016 | Dempsey |
| 9,446,263 B2 | 9/2016 | Dempsey |
| 9,472,000 B2 | 10/2016 | Dempsey |
| 9,498,167 B2 | 11/2016 | Mostafavi |
| 9,526,918 B2 | 12/2016 | Kruip |
| 9,675,271 B2 | 6/2017 | Shvartsman |
| 2001/0049475 A1 | 12/2001 | Bucholz |
| 2002/0046010 A1 | 4/2002 | Wessol |
| 2002/0091315 A1 | 7/2002 | Spetz |
| 2002/0131556 A1 | 9/2002 | Steinberg |
| 2002/0150207 A1 | 10/2002 | Kapatoes |
| 2002/0151786 A1 | 10/2002 | Shukla |
| 2002/0193685 A1 | 12/2002 | Mate |
| 2003/0011451 A1 | 1/2003 | Katznelson |
| 2003/0057947 A1 | 3/2003 | Ni |
| 2003/0068097 A1 | 4/2003 | Wilson |
| 2003/0083901 A1 | 5/2003 | Bosch |
| 2003/0086526 A1 | 5/2003 | Clark |
| 2003/0094947 A1 | 5/2003 | Akgun |
| 2003/0112107 A1 | 6/2003 | Forbes |
| 2003/0112922 A1 | 6/2003 | Burdette |
| 2003/0155530 A1 | 8/2003 | Adnani |
| 2003/0181804 A1 | 9/2003 | Gagnon |
| 2003/0197507 A1 | 10/2003 | Liu |
| 2003/0219098 A1 | 11/2003 | McNutt |
| 2004/0030240 A1 | 2/2004 | Kimura |
| 2004/0054248 A1 | 3/2004 | Kimchy |
| 2004/0106869 A1 | 6/2004 | Tepper |
| 2004/0239327 A1 | 12/2004 | Heid |
| 2004/0254448 A1 | 12/2004 | Amies |
| 2004/0254773 A1 | 12/2004 | Zhang |
| 2005/0020917 A1 | 1/2005 | Scherch |
| 2005/0030028 A1 | 2/2005 | Clarke |
| 2005/0053267 A1 | 3/2005 | Mostafavi |
| 2005/0054916 A1 | 3/2005 | Mostafavi |
| 2005/0065431 A1 | 3/2005 | Reiderman |
| 2005/0077899 A1 | 4/2005 | Jacobs |
| 2005/0143965 A1 | 6/2005 | Failla |
| 2005/0197564 A1 | 9/2005 | Dempsey |
| 2005/0197654 A1 | 9/2005 | Edman |

(56) References Cited

U.S. PATENT DOCUMENTS

| | | | |
|---|---|---|---|
| 2005/0201516 A1 | 9/2005 | Ruchala | |
| 2005/0207531 A1 | 9/2005 | Dempsey | |
| 2005/0254623 A1 | 11/2005 | Kamath | |
| 2006/0033496 A1 | 2/2006 | Shvartsman | |
| 2006/0058636 A1 | 3/2006 | Wemple | |
| 2006/0074292 A1 | 4/2006 | Thomson | |
| 2006/0120583 A1 | 6/2006 | Dewaele | |
| 2006/0170679 A1 | 8/2006 | Wang | |
| 2006/0193441 A1 | 8/2006 | Cadman | |
| 2006/0280287 A1 | 12/2006 | Esham | |
| 2006/0291621 A1 | 12/2006 | Yan | |
| 2007/0003021 A1 | 1/2007 | Guertin | |
| 2007/0016014 A1 | 1/2007 | Hara | |
| 2007/0038058 A1 | 2/2007 | West | |
| 2007/0043286 A1 | 2/2007 | Lu | |
| 2007/0052420 A1 | 3/2007 | Speck | |
| 2007/0053492 A1 | 3/2007 | Kidani | |
| 2007/0083114 A1 | 4/2007 | Yang | |
| 2007/0086569 A1* | 4/2007 | Johnsen | A61N 5/1045 378/65 |
| 2007/0197908 A1 | 8/2007 | Ruchala | |
| 2007/0230770 A1 | 10/2007 | Kulkarni | |
| 2007/0244386 A1 | 10/2007 | Steckner | |
| 2008/0024130 A1 | 1/2008 | Schlueter | |
| 2008/0033287 A1 | 2/2008 | Schwarze | |
| 2008/0049897 A1* | 2/2008 | Molloy | A61N 5/1042 378/65 |
| 2008/0093567 A1 | 4/2008 | Gall | |
| 2008/0108894 A1 | 5/2008 | Elgavish | |
| 2008/0116894 A1 | 5/2008 | Weiger | |
| 2008/0123927 A1 | 5/2008 | Miga | |
| 2008/0177138 A1 | 7/2008 | Courtney | |
| 2008/0197842 A1 | 8/2008 | Lustig | |
| 2008/0208036 A1 | 8/2008 | Amies | |
| 2008/0235052 A1 | 9/2008 | Node-Langlois | |
| 2008/0303457 A1 | 12/2008 | Maltz | |
| 2009/0039886 A1 | 2/2009 | White | |
| 2009/0060130 A1 | 3/2009 | Wilkens | |
| 2009/0129545 A1 | 5/2009 | Adler | |
| 2009/0129659 A1 | 5/2009 | Deutschmann | |
| 2009/0147916 A1 | 6/2009 | Fallone | |
| 2009/0149735 A1 | 6/2009 | Fallone | |
| 2009/0161826 A1 | 6/2009 | Gertner | |
| 2009/0171184 A1 | 7/2009 | Jenkins | |
| 2009/0175418 A1 | 7/2009 | Sakurai | |
| 2009/0264768 A1 | 10/2009 | Courtney | |
| 2010/0033186 A1 | 2/2010 | Overweg | |
| 2010/0049030 A1 | 2/2010 | Saunders | |
| 2010/0056900 A1 | 3/2010 | Whitcomb | |
| 2010/0113911 A1 | 5/2010 | Dempsey | |
| 2010/0119032 A1 | 5/2010 | Yan | |
| 2010/0239066 A1 | 9/2010 | Fahrig | |
| 2010/0312095 A1 | 12/2010 | Jenkins | |
| 2010/0312100 A1 | 12/2010 | Zarkh | |
| 2010/0322497 A1 | 12/2010 | Dempsey | |
| 2011/0012593 A1* | 1/2011 | Shvartsman | G01R 33/28 324/307 |
| 2011/0051893 A1 | 3/2011 | McNutt | |
| 2011/0118588 A1 | 5/2011 | Komblau | |
| 2011/0121832 A1 | 5/2011 | Shvartsman | |
| 2011/0142887 A1 | 6/2011 | Har-Noy | |
| 2011/0150180 A1* | 6/2011 | Balakin | G21K 1/087 378/65 |
| 2011/0204262 A1 | 8/2011 | Pu | |
| 2011/0218420 A1 | 9/2011 | Carlone | |
| 2011/0237859 A1 | 9/2011 | Kuhn | |
| 2011/0241684 A1 | 10/2011 | Dempsey | |
| 2011/0284757 A1 | 11/2011 | Butuceanu | |
| 2011/0304416 A1 | 12/2011 | Warner | |
| 2012/0019246 A1 | 1/2012 | Kannengiesser | |
| 2012/0022363 A1 | 1/2012 | Dempsey | |
| 2012/0043482 A1 | 2/2012 | Prince | |
| 2012/0070056 A1 | 3/2012 | Krueger | |
| 2012/0150017 A1 | 6/2012 | Yamaya | |
| 2012/0157402 A1 | 6/2012 | Cao | |
| 2012/0165652 A1 | 6/2012 | Dempsey | |
| 2012/0230462 A1 | 9/2012 | Robar | |
| 2012/0245453 A1 | 9/2012 | Tryggestad | |
| 2012/0253172 A1 | 10/2012 | Loeffler | |
| 2013/0066135 A1 | 3/2013 | Rosa | |
| 2013/0086163 A1 | 4/2013 | Neff | |
| 2013/0090547 A1 | 4/2013 | Bani-Hashemi | |
| 2013/0090549 A1* | 4/2013 | Meltsner | G16H 50/50 600/411 |
| 2013/0147476 A1 | 6/2013 | Shvartsman | |
| 2013/0225975 A1 | 8/2013 | Harvey | |
| 2013/0245425 A1 | 9/2013 | Dempsey | |
| 2013/0261429 A1 | 10/2013 | Lee | |
| 2013/0261430 A1 | 10/2013 | Uhlemann | |
| 2013/0296687 A1 | 11/2013 | Dempsey | |
| 2013/0345545 A1 | 12/2013 | Gross | |
| 2013/0345556 A1 | 12/2013 | Courtney | |
| 2014/0003023 A1 | 1/2014 | Weibler | |
| 2014/0010355 A1 | 1/2014 | Seeber | |
| 2014/0077098 A1 | 3/2014 | Tachikawa | |
| 2014/0084926 A1 | 3/2014 | Amthor | |
| 2014/0112453 A1 | 4/2014 | Prince | |
| 2014/0121495 A1 | 5/2014 | Dempsey | |
| 2014/0128719 A1 | 5/2014 | Longfield | |
| 2014/0135615 A1 | 5/2014 | Krulp | |
| 2014/0263990 A1 | 9/2014 | Kawrykow | |
| 2014/0266206 A1 | 9/2014 | Dempsey | |
| 2014/0266208 A1* | 9/2014 | Dempsey | A61N 5/1049 324/322 |
| 2014/0275963 A1 | 9/2014 | Shvartsman | |
| 2014/0330108 A1 | 11/2014 | Dempsey | |
| 2014/0336442 A1 | 11/2014 | Keppel | |
| 2014/0347053 A1 | 11/2014 | Dempsey | |
| 2015/0065860 A1 | 3/2015 | Shvartsman | |
| 2015/0077118 A1 | 3/2015 | Shvartsman | |
| 2015/0095044 A1* | 4/2015 | Hartman | G16H 50/20 705/2 |
| 2015/0154756 A1 | 6/2015 | Gerganov | |
| 2015/0165233 A1 | 6/2015 | Dempsey | |
| 2015/0185300 A1 | 7/2015 | Shvartsman | |
| 2015/0251020 A1 | 9/2015 | Calone | |
| 2015/0273239 A1 | 10/2015 | Hsu | |
| 2016/0011288 A1 | 1/2016 | Overweg | |
| 2016/0067525 A1 | 3/2016 | Bouchet | |
| 2016/0146911 A1 | 5/2016 | Chmielewski | |
| 2016/0184609 A1 | 6/2016 | Dempsey | |
| 2016/0232690 A1 | 8/2016 | Ahmad | |
| 2016/0256712 A1 | 9/2016 | Vahala | |
| 2016/0278719 A1 | 9/2016 | Jensen | |
| 2016/0334479 A1 | 11/2016 | Poole | |
| 2016/0356869 A1 | 12/2016 | Dempsey | |
| 2017/0001039 A1* | 1/2017 | Dempsey | A61N 5/1049 |
| 2017/0014644 A1* | 1/2017 | Shvartsman | G01R 33/3806 |
| 2017/0021198 A1* | 1/2017 | Kawrykow | A61B 5/055 |
| 2017/0120075 A1 | 5/2017 | Overweg | |
| 2017/0148536 A1 | 5/2017 | Kawrykow | |
| 2017/0176556 A1 | 6/2017 | Shvartsman | |
| 2017/0203126 A1 | 7/2017 | Dempsey | |
| 2017/0231583 A1* | 8/2017 | Goteti Venkata | A61B 6/5258 600/427 |
| 2017/0252577 A1* | 9/2017 | Dempsey | A61N 5/1031 |
| 2017/0371001 A1 | 12/2017 | Dempsey | |
| 2018/0003789 A1 | 1/2018 | Amthor | |
| 2018/0021595 A1* | 1/2018 | Kesti-Helia | A61N 5/103 600/1 |
| 2018/0078785 A1* | 3/2018 | Ollila | A61N 5/1039 |
| 2018/0078792 A1* | 3/2018 | Ollila | A61N 5/1031 |
| 2018/0133511 A1 | 5/2018 | Dempsey | |
| 2018/0185669 A1* | 7/2018 | Kuusela | A61N 5/1031 |
| 2018/0243584 A1* | 8/2018 | Nord | A61N 5/1036 |
| 2019/0004131 A1 | 1/2019 | Wachowicz | |
| 2019/0060670 A1 | 2/2019 | Ni | |
| 2019/0083814 A1* | 3/2019 | Tallinen | A61N 5/1031 |
| 2019/0090777 A1 | 3/2019 | Leghissa | |
| 2019/0168028 A1 | 6/2019 | Dempsey | |
| 2019/0217126 A1 | 7/2019 | Shvartsman | |
| 2019/0353724 A1 | 11/2019 | Snelten | |
| 2019/0353725 A1 | 11/2019 | Dempsey | |

(56) References Cited

U.S. PATENT DOCUMENTS

| | | |
|---|---|---|
| 2020/0086143 A1 | 3/2020 | Maltz |
| 2020/0147412 A1 | 5/2020 | Ni |
| 2020/0246637 A1 | 8/2020 | Wang |

FOREIGN PATENT DOCUMENTS

| | | |
|---|---|---|
| CN | 1669599 A | 9/2005 |
| CN | 1946339 | 4/2007 |
| CN | 1946339 A | 4/2007 |
| CN | 101000689 A | 7/2007 |
| CN | 101267858 A | 9/2008 |
| CN | 101268474 A | 9/2008 |
| CN | 101278361 A | 10/2008 |
| CN | 101309726 A | 11/2008 |
| CN | 101443819 A | 5/2009 |
| CN | 101452065 A | 6/2009 |
| CN | 102247658 A | 11/2011 |
| CN | 102369529 A | 3/2012 |
| CN | 102472830 A | 5/2012 |
| CN | 102641561 A | 8/2012 |
| CN | 102713682 A | 10/2012 |
| DE | 3828639 A1 | 3/1989 |
| EP | 0152554 A2 | 8/1985 |
| EP | 2230530 A1 | 9/2010 |
| EP | 2359905 A1 | 8/2011 |
| EP | 2424430 B1 | 1/2013 |
| FR | 2839894 A1 | 11/2003 |
| GB | 2393373 A | 3/2004 |
| JP | 63294839 | 12/1988 |
| JP | H03243877 A | 10/1991 |
| JP | 06054916 | 1/1994 |
| JP | H07148142 A | 6/1995 |
| JP | H07213507 A | 8/1995 |
| JP | 2001517132 | 10/2001 |
| JP | 2001517132 A | 10/2001 |
| JP | 2002186676 A | 7/2002 |
| JP | 2002522129 A | 7/2002 |
| JP | 2004351207 A | 12/2004 |
| JP | 2005103295 A | 4/2005 |
| JP | 2006149560 A | 6/2006 |
| JP | 2007526036 A | 9/2007 |
| JP | 2008194449 | 8/2008 |
| JP | 2008532681 A | 8/2008 |
| JP | 2009501043 | 1/2009 |
| JP | 2009501043 A | 1/2009 |
| JP | 2009511222 A | 3/2009 |
| JP | 2009112870 A | 5/2009 |
| JP | 2009160309 | 7/2009 |
| JP | 2009160309 A | 7/2009 |
| JP | 2009538195 | 11/2009 |
| JP | 2010269067 A | 12/2010 |
| JP | 6224020 | 7/2015 |
| JP | 2015520631 | 7/2015 |
| WO | 1993018707 | 9/1993 |
| WO | 1999032189 | 7/1999 |
| WO | 1999032189 A1 | 7/1999 |
| WO | 2000025864 | 5/2000 |
| WO | 2002072190 A2 | 9/2002 |
| WO | 20030008986 | 1/2003 |
| WO | 2004024235 A1 | 3/2004 |
| WO | 2005081842 A2 | 9/2005 |
| WO | 2006007277 A2 | 1/2006 |
| WO | 2006097274 A1 | 9/2006 |
| WO | 2006097864 A1 | 9/2006 |
| WO | 2007007276 A2 | 1/2007 |
| WO | 2007012933 A2 | 2/2007 |
| WO | 2007014105 A2 | 2/2007 |
| WO | 2007045076 A1 | 4/2007 |
| WO | 2007126842 A2 | 11/2007 |
| WO | 2008013598 A2 | 1/2008 |
| WO | 2008122899 A1 | 10/2008 |
| WO | 2009004521 A2 | 1/2009 |
| WO | 2009107005 A2 | 9/2009 |
| WO | 2009155700 A1 | 12/2009 |
| WO | 2010103644 | 9/2010 |
| WO | 2010103644 A1 | 9/2010 |
| WO | 2010113050 A2 | 10/2010 |
| WO | 2011008969 A1 | 1/2011 |
| WO | 2011063342 A1 | 5/2011 |
| WO | 2012045153 | 4/2012 |
| WO | 2012164527 A1 | 12/2012 |
| WO | 2015085008 A1 | 6/2015 |
| WO | 20150138945 | 9/2015 |

OTHER PUBLICATIONS

English machine translation of JP63-294839 (1998), as provided by the Japanese Patent Office, English Abstract.

Office Action dated Apr. 17, 2019 for U.S. Appl. No. 15/268,366 (pp. 1-6).

Notice of Allowance dated May 9, 2019 for U.S. Appl. No. 15/445,832 (pp. 1-5).

Office Action dated Jun. 25, 2019 for U.S. Appl. No. 13/462,750 (pp. 1-15).

Notice of Allowance dated Jul. 1, 2019 for U.S. Appl. No. 15/268,366 (pp. 1-5).

Office Action dated Feb. 20, 2018 for U.S. Appl. No. 15/436,620 (pp. 1-25).

Office Action dated Jan. 28, 2019 for U.S. Appl. No. 15/436,620 (pp. 1-17).

Webb, Steve, 'Intensity-modulated radiation therapy using only jaws and a mask: II. A simplified concept of relocatable single-bixel attenuators', published May 22, 2002, Institute of Physics Publishing, Physics in Medicine and Biology, Phys. Med. Biol. 47 (2002) 1869-1879.

Tamada and Kose. 'Two-Dimensional Compressed Sensing Using the Cross-sampling Approach for Low-Field MRI Systems.' IEEE Transactions on Medical Imaging. vol. 33, No. 9. Sep. 2014. pp. 1905-1912.

Bernier, Jacques et al. 'Radiation oncology: a century of achievements' Nature Reviews-Cancer, vol. 4, Sep. 2004. pp. 737-747.

Buchanan, Roger 'Cobalt on the way out' British Medical Journal, vol. 292, Feb. 1, 1986. p. 290.

De Poorter J. et al. 'Noninvasive MRI Thermometry with the Proton Resonance Frequencey (PRF) Method: In Vivo Results in Human Muscle,' Magnetic Resonance in Medicine, Academic Press, Duluth, vol. 33, No. 1, Jan. 1995 pp. 74-81 XP000482971.

Goldberg, S. Nahum; G. Scott Gazelle, and Peter R. Mueller. 'Thermal Ablation Therapy for Focal Malignancy: A Unified Approach to Underlying Principles, Techniques, and Diagnostic Imaging Guidance.' Amer. J. of Roentgenology, vol. 174, Feb. 2000 pp. 323-331 XP002431995.

Jursinic, Paul et al. 'Characteristics of secondary electrons produced by 6, 10 and 24 MV x-ray beams' Phys. Med. Biol. 41 (1996) 1499-1509, United Kingdom.

Khan, Faiz M., 'The Physics of Radiation Therapy (second edition)', Lippincott Williams & Wilkins. Chapter 13. 1985. pp. 323-332.

Liang, J. and D. Yan. 'Reducing Uncertainties in Volumetric Image Based Deformable Organ Registration.' Medical Physics, vol. 30, No. 8, 2003, pp. 2116-2122.

Raaymakers, B.W. et al. 'Integrating a MRI scanner with a 6 MV radiotherapy accelerator: dose deposition in a transverse magnetic field', Phys. Med. Biol. 49 (2004) 4109-4118.

Schreiner, L. John, et al. 'The role of Cobalt-60 in modern radiation therapy: Dose delivery and image guidance'. Journal of Medical Physics, vol. 34, No. 3, 2009, 133-136.

Tokuda, Junichi; Morikawa, Shigehiro; Dohi, Takeyoshi; Hata, Nobuhiko; Motion Tracking in MR-Guided Liver Therapy by Using Navigator Echoes and Projection Profile Matching, 2004. vol. 11. No. 1. pp. 111-120.

Schreiner, John; Kerr, Andrew; Salomons, Greg; Dyck, Christine, and Hajdok, George, 'The Potential for Image Guided Radiation Therapy with Cobalt-60 Tomotherapy', MICCAI 2003, LNCS 2879, pp. 449-456, 2003.

Balter, James M., et al. 'Accuracy of a Wireless Localization System for Radiotherapy' Int. J. Radiation Oncology Biol. Phys., vol. 61, No. 3. pp. 933-937, Nov. 1, 2004, Elsevier Inc., USA.

(56) References Cited

OTHER PUBLICATIONS

Baro, J et al. 'Penelope: An algorithm for Monte Carlo simulation of the penetration and energy loss of electrons and positrons in matter' Nuclear Instruments and Methods in Physics Research B 100 (1995) 31-46, received Sep. 30, 1994, Elsevier Science B.V.
Chng, N. et al. 'Development of inverse planning and limited angle CT reconstruction for cobalt-60 tomotherapy' Proceedings of 51st Annual Meeting of Canadian Organization of Medical Physicists and the Canadian College of Physicists in Medicine, 2005, McMaster University, Hamilton Ontario. Medical Physics, 2005, p. 2426.
Goitein, Michael. 'Organ and Tumor Motion: An Overview.' Seminars in Radiation Oncology. vol. 14, No. 1 Jan. 2004: pp. 2-9.
Hajdok, George. 'An Investigation of Megavoltage Computed Tomography Using a Radioactive Cobalt-60 Gamma Ray Source for Radiation Therapy Treatment Verification.' Thesis. May 2002. 150 pages.
Langen, K.M. et al. 'Organ Motion and its Management.' Int J. Radiation Oncology Biol. Phys., vol. 50, No. 1, pp. 265-278. 2001. Elsevier Science Inc., USA.
Lurie, D.J., PhD. 'Free radical imaging' The British Journal of Radiology. 74 (2001). pp. 782-784.
Raaijmakers, A.J.E. et al. 'Integrating a MRI scanner with a 6 MV radiotherapy accelerator: dose increase at tissue-air interfaces in a lateral magnetic field due to returning electrons.' Phys. Med. Biol. 50 (2005) pp. 1363-1376.
Sempau, Josep et al. 'DPM, a fast, accurate Monte Carlo code optimized for photon and electron radiotherapy treatment planning dose calculations.' Phys. Med. Biol. 45 (2000) pp. 2263-2291, Received Feb. 29, 2000. Printed in the UK.
Jaffray, David A., et al. 'Flat-Panel Cone Beam Computed Tomography for Image-Guided Radiation Therapy' Int. J. Radiation Oncology Biol. Phys., vol. 53, No. 5, pp. 1337-1349, Apr. 3, 2002, Elsevier Science Inc., USA.
Lopez, Mike R. et al. 'Relativistic Magnetron Driven by a Microsecond E-Beam Accelerator with a Ceramic Insulator' IEEE Transactions on Plasma Science vol. 32, No. 3, Jun. 2004. pp. 1171-1180.
Wazer, David E. et al. 'Principles and Practice of Radiation Oncology (fifth edition).', Wolters Kluwer/Lippincott Williams & Wilkins. 2008. 2 pages.
Sherouse, George W. et al. 'Virtual Simulation in the Clinical Setting: Some Practical Considerations', Int. J. Radiation Oncology Biol. Phys. vol. 19, pp. 1059-1065, Apr. 26, 1990, Pergamon Press, USA.
Warrington, Jim et al. 'Cobalt 60 Teletherapy for Cancer: A Revived Treatment Modality for the 21st Century', 2002 The Institution of Electrical Engineers, pp. 19-1-19/19.
EP App. No. 10195476.6; Extended EP Search Report dated Jul. 4, 2011; 11 pages.
Webb, S. 'The physical basis of IMRT and inverse planning' The British Journal of Radiology, 76 (2003), 678-689, 2003 The British Institute of Radiology.
EP App. No. 10800553.9; Extended EP Search Report dated Oct. 17, 2013; 10 pages.
PCT App. No. PCT/US2010/042156; International Search Report and Written Opinion dated Sep. 10, 2010; 15 pages.
St. Aubin et al,, 'Magnetic decoupling on the linac in a low field biplanar linac-MR system', Med. Phys, 37 (9), Sep. 2010, pp. 4755-4761.
Lagendijk et al, 'MRI/linac integration', Radiotherapy and Oncology, Elsevier, Ireland, (Nov. 26, 2007), vol. 86, No. 1, doi:10.1016/J.RADONC.2007.10.034, ISSN 0167-8140, pp. 25-29, XP022423061.
Overweg et al. 'System for MRI guided Radiotherapy.' Proc. Intl. Soc. Mag. Reson. Med. 17(2009):594.
Partial International Search Report Issued in International Application No. PCT/US2013/039009, dated Oct. 18, 2013.
Lagendijk JJ W et al.: "MRI Guided Radiotherapy: A MRI based linear Accelerator", Radiotherapy and Oncology, vol. 56, No. 01, Sep. 21, 2000 (Sep. 21, 2009), pp. S60-S61.
Hong J et al, 'Interventional navigation for abdominal therapy based on simultaneous use of MRI and ultrasound', Medical and Biological Engineering and Computing, Springer, Heildelberg, DE, vol. 44, No. 12, doi:10.1007/S11517-006-0133-2, ISSN 0140-0118, (Nov. 11, 2006), pp. 1127-1134, (Nov. 11, 2006), XP001551805.
Nomayr A et al.; 'MRI appearance of radiation-induced changes of normal cervical tissues', Eur Radiol., (2001), vol. 11, No. 9, doi:doi:10.1007/s003300000728, pp. 1807-1817, XP055095676.
Hicks, et al., 'Early FDG-PET imaging after radical radiotherapy for non-small-cell lung cancer: Inflammatory changes in normal tissues correlate with tumor response and do not confound therapeutic response evaluation', International Journal of Radiation: Oncology Biology Physics; [Publication // Division of Scientific and Technical Information, International Atomic Energy Agency, ISSN 0074-1876; 1196], Pergamon Press, USA, (Oct. 1, 2004), vol. 60, No. 2, doi:10.1016/J.IJROBP.2004.03.036, ISSN 0360-3016.
Rancati et al., NTCP Modeling of Subacute/Late Laryngeal Edema Scored by Fiberoptic Examination, Int. J. Radiation Oncology Biol. Rhys., vol. 75, No. 3, pp. 915-923, 2009.
Golen et al., "A comparison of two scoring systems for late radiation toxicity in patients after radiotherapy for head and neck cancer," Rep Pract Oncol Radiother, 2005; 10(4): 179-192.
Sanguineti et al., Dosimetric Predictors of Laryngeal Edema, Int. J. Radiation Oncology Biol. Phys., vol. 68, No. 3, pp. 741-749, 2007.
International Search Report of the International Searching Authority issued in International Application No. PCT/US2014/028792, dated Jul. 2, 2014.
EP App. No. 17000760.3; Extended EP Search Report dated Nov. 9, 2017.
Mah et al., "Measurement of intrafractional prostate motion using magnetic resonance imaging," Int. J. Radiation Oncology Boil. Phys. Vo.54, No. 2, pp. 568-575, 2002.
PCT App. No. PCT/US2017/020015; International Search Report and Written Opinion dated Jul. 26, 2017; 18 pages.
Office Action dated Oct. 22, 2018 for U.S. Appl. No. 15/268,366 (pp. 1-8).
Office Action dated Nov. 15, 2018 for U.S. Appl. No. 15/242,449 (pp. 1-12).
Office Action dated Jan. 14, 2019 for U.S. Appl. No. 15/445,832 (pp. 1-11).
Office Action dated Mar. 7, 2019 for U.S. Appl. No. 13/462,750 (pp. 1-11).
May et al., Abnormal Signal Intensity in Skeletal Muscle at MR Imaging: Patterns, Pearls, and Pitfalls, RadioGraphics 2000; 20: S295-S315.
Pasternak et al., Free Water Elimination and Mapping from Diffusion, Magnetic Resonance in Medicine 62:717-730, 2009.
Wang et al., Evolution of Radiation-Induced Brain Injury: MRI Imaging—Based Study, Radiology: vol. 254: No. 1; Jan. 2010.
McMahon et al., Muscle Edema, AJR:194, Apr. 2010, W284-W292.
B W Raaymakers et al.; "Integrating a 1.5 T MRI Scanner with a 6 MV Accelerator: Proof of Concepts," Physics in Medicine and Biology. vol. 54, No. 12, May 19, 2009, pp. N229-N237, XP055395399, Bristol GB ISSN: 0031-9155.
Barth, et al. "Simultaneous Multislice (SMS) Imaging Techniques." Magnetic Resonance in Medicine; vol. 75; pp. 63-81; 2016.
Bilgin, A. et al. 'Randomly Perturbed Radial Trajectories for Compressed Sensing MRI.' Proceedings of International Society for Magnetic Resonance in Medicine 16 (2008):p. 3152.
Blaimer, et al. 'Smash, Sense, Pills, Grappa, How to Choose the Optimal Method'. Top Magan Reson Imaging, vol. 15, No. 4, Aug. 2004, pp. 223-236.
Candes, et al. 'Robust Uncertainty Principles: Exact Signal Reconstruction from Highly Incomplete Frequency Information.' IEEE Transactions on Information Theory, vol. 52, No. 2, Feb. 2006, pp. 489-509.
Candes, et al. 'Sparsity and Incoherence in Compressive Sampling'. Electrical and Computer Engineering, Georgia Tech, Atlanta, GA, 90332. Nov. 2006, pp. 1-20.
CIPRA 'L1-magic' from SIAM News, vol. 39, No. 9, Nov. 2006. (3 pages).
Donoho, David L., 'Compressed Sensing'. Department of Statistics, Stanford University. Sep. 14, 2004. (34 pages).

(56) References Cited

OTHER PUBLICATIONS

Foroosh, Hassan, et.al. 'Extension of Phase Correlation to Subpixel Registration.' IEEE Transactions on Image Processing, vol. 11, No. 3, 2002, pp. 188-200.
Gerganov G et al, 'Portal image registration using the phase correlation method', 2013 IEEE Nuclear Science Symposium and Medical Imaging Conference (2013 NSS/MIC), IEEE, (Oct. 27, 2013), doi:10.1109/NSSMIC.2013.6829306, pp. 1-3, XP032601397.
Green et al. 'Split cylindrical gradient coil for combined PET-MR system.' Proc. Intl. Soc. Mag. Reson. Med. 16 (2008):352.
Haacke, Mark E. et al. 'Constrained reconstruction: A superresolution, optimal signal-to-noise alternative to the Fourier transform in magnetic resonance imaging.' Medical Physics, AIP, Melville, NY, US, vol. 16, No. 3, May 1, 1989 (May 1, 1989), pp. 388-397, XP000034068, ISSN: 0094-2405, DDI: 10.1118/1.596427.
Hernando, D. et al. 'Interventional MRI with sparse sampling: an application of compressed sensing.' Proceedings of International Society for Magnetic Resonance in Medicine.16 (2008):p. 1482.
International Search Report and Written Opinion dated Apr. 13, 2012, for corresponding international application No. PCT/US2011/066605; 9 pages.
International Search Report issued by the European Patent Office in International Application No. PCT/US2014/023556 dated Jul. 18, 2014. 6 pages.
Irarrazabal, Pablo, and Dwight G. Nishimura. 'Fast Three Dimensional Magnetic Resonance Imaging.' Magnetic Resonance in Medicine, vol. 33, No. 5, 1995, pp. 656-662.
Jan J. W. Lagendijk et al.; "MR Guidance in Radiotherapy", Physics in Medicine and Biology, Institute of Physics Publishing, Bristol GB, vol. 59, No. 21, Oct. 16, 2014, pp. R349-R369, XP020272054, ISSN: 0031-9155.
Law, C., and Glover, G. 'Deconvolving Haemodynamic Response Function in fMRI under high noise by Compressive Sampling.' Proceedings of International Society for Magnetic Resonance in Medicine. 17 (2009):p. 1712. Stanford University, Stanford, CA, United States.
Li, Kang and Kanadae, Takeo. 'Nonnegative Mixed-Norm Preconditioning for Microscopy Image Segmentation.' Information Processing in Medical Imaging. Springer Berlin Heidelberg. vol. 5636. (2009):362-373.
Lucas et al. 'Simultaneous PET-MR: toward a combined microPET. RTM.-MR system.' Proc. Intl. Soc. Mag. Reson. Med. 15(2007):922.
Lustig, et al. 'L1 SPIR-IT: Autocalibrating Parallel Imaging Compressed Sensing.' Electrical Engineering, Stanford University, Stanford, CA, United States. Radiology. Stanford University. Statistics, Stanford University (p. 334).
Lustig, M, et. al. 'Faster Imaging with Randomly Perturbed, Undersampled Spirals and |L|_1 Reconstruction.' In: Proceedings of the 13th Annual Meeting of ISMRM, Miami Beach, 2005. (1 page).
Macura, Katarzyna J., MD, PhD. 'Advancements in Magnetic Resonance-Guided Robotic Interventions in the Prostate'. Top Magn Reson Imaging. vol. 19, No. 6. Dec. 2008. pp. 297-304.
Medtronic, Inc.. 'Image-Guided Surgery Overview'. 2010. 2 pages.
Meyer, et al. "Fast Spiral Coronary Artery Imaging", Magnetic Resonance in Medicine 28, pp. 202-213 (1992).
Mozer, Pierre C, MD, PhD. 'Robotic Image-Guided Needle Interventions of the Prostate'. Reviews in Urology. vol. 11, No. 1. 2009. pp. 7-15.
Muntener, Michael, MD et al. 'Transperineal Prostate Intervention: Robot for fully Automated MR Imaging-System Description and Proof of Principle in a Canine Model'. Radiology. vol. 247, No. 2. May 2008. pp. 543-549.
Notice of Allowance dated Apr. 17, 2019 for U.S. Appl. No. 15/449,774 (pp. 1-5).
Patriciu, Alexandru, et al., 'Automatic Brachytherapy Seed Placement Under MRI Guidance'. IEEE Transactions on Biomedical Engineering. vol. 54, No. 8. Aug. 2007. pp. 1-8.
PCT App. No. PCT/US2010/039036; International Search Report dated Aug. 11, 2010; (pp. 1-2).
PCT App. No. PCT/US2016/063416; International Preliminary Report on Patentability and International Search Report with Written Option dated Jun. 7, 2018; 9 pages.
PCT App. No. PCT/US2017/038867; International Search Report and Written Opinion dated Nov. 8, 2017; (pp. 1-12).
Reddy, B. Srinivasa, and B. N. Chatterji. 'An FFT-Based Technique for Translation, Rotation, and Scale-Invariant Image Registration.' IEEE Transactions on Image Processing, vol. 5, No. 8, Aug. 1996, pp. 1266-1271.
Riek, et al. "Flow Compensation in MRI Using a Phase-Corrected Real Reconstruction", Magnetic Resonance in Medicine 30, pp. 724-731, 1993.
Roullot Elodie et al. 'Regularized reconstruction of 3D high-resolution magnetic resonance images from acquisitions of anisotropically degraded resolutions.' Pattern Recognition, 2000. Proceedings. 15th International Conference on Sep. 3-7, 2000; [Proceedings of the International Conference on Pattern Recognition. (ICPR)], Los Alamitos, CA, USA,IEEE Comput. Soc, US, vol. 3, Sep. 3, 2000 (Sep. 3, 2000), pp. 346-349.
Shvartsman et al. 'Gradient Coil Induced Eddy Current Computation Using the Boundary Elements Method.' Proc. Intl. Soc. Mag. Reson. Med. 17(2009):3055.
Stoianovici, Dan, et al. MRI Stealth Robot for Prostate Interventions. Minimally Invasive Therapy. 2007. pp. 241-248.
Tokuda, J. et al. 'Real-Time Organ Motion Tracking and Fast Image Registration System for MRI-Guided Surgery.' Systems and Computers in Japan Scripta Technica USA. vol. 37, No. 1. Jan. 2006: 83-92. Database Inspec [Online]. The Institution of Electrical Engineers, Stevenage, GB; Jan. 2006.
Trzasko et al. 'Highly Undersampled Magnetic Resonance Image Reconstruction via Homotopic L0—Minimization' IEEE Transactions on Medical Imaging. vol. 28. No. 1. Jan. 31, 2009, pp. 106-121.
Weaver, John B.; "Simultaneous Multislice Acquisition of MR Images", Magnetic Resonance in Medicine, John Wiley & Sons, Inc., vol. 8, No. 3, Nov. 1, 1988, pp. 275-284, XP000003030, ISSN: 0740-3194.
Webb, Steve. "Historical Perspective on IMRT." Institute of Cancer Research and Royal Marsden NHS Trust. 2002. (23 pages).
Yang, Junfeng, et. al. 'A Fast TVL1-L2 Minimization Algorithm for Signal Reconstruction from Rartial Fourier Data.' Technical Report, TR08-27, CAAM, Rice University Houston, TX, 2008. pp. 1-10.
Zaitsev M et al.: "Shared k-space Echo Planar Imaging with Keyhole," Magnetic Resonance in Medicine, John Wiley & Sons, Inc. US, vol. 45, Jan. 1, 2001, pp. 109-117, XP002311925, ISSN: 0740-3194.
Zitova B et al, 'Image Registration Methods: A Survey', Image and Vision Computing, Elsevier, Guildford, GB, (Oct. 1, 2003), vol. 21, No. 11, doi:10.1016/S0262-8856(03)00137-9, ISSN 0262-8856, pp. 977-1000, XP001189327.

\* cited by examiner

RADIOTHERAPY SYSTEMS, METHODS AND SOFTWARE

RELATED APPLICATIONS

This application claims priority to and the benefit of U.S. Provisional Application No. 62/595,478, filed Dec. 6, 2017, which is hereby incorporated by reference in its entirety.

BACKGROUND

Radiotherapy uses beams of radiation to kill cells to treat disease, typically proliferative tissue disorders such as cancer. Radiotherapy can be used to treat targets in patients requiring a dose of ionizing radiation for curative effect, such as grossly observable tumors, anatomic regions containing microscopic disease or potential disease spread, or regions that include margins for motion and/or delivery uncertainties. The ionizing radiation delivered by radiotherapy beams destroys the DNA and other important components of diseased cells and prevents the cells from replicating.

Typical radiotherapy involves treatment planning to determine how to deliver the prescribed radiation dose to the target, while at the same time sparing healthy tissues in the vicinity by limiting doses below acceptable thresholds to prevent deadly or debilitating side effects.

SUMMARY

Radiation therapy systems (e.g., photon therapy delivery systems) are disclosed for delivery of radiation therapy to a patient (e.g., via a photon beam). Certain embodiments may include a controller configured to facilitate delivery of radiation therapy via a photon beam and also a particle beam.

The delivery of radiation therapy with the photon beam and the delivery of radiation therapy via a particle beam can both be completed without having to move the patient. The photon therapy delivery system can be configured to deliver radiation therapy to a patient via photon beams from multiple directions. Also, the system can include a magnetic resonance imaging system (MRI) configured to acquire images of the patient during administration of radiation therapy.

Also disclosed are computer program products that allow the receiving of radiation therapy beam information for a radiation therapy treatment of a patient utilizing a particle beam and a photon beam. Patient magnetic resonance imaging (MRI) data can be received during the radiation therapy treatment. Further, the patient MRI data can be utilized to perform real-time calculations of a location of dose deposition for the particle beam and for the photon beam, taking into account interaction properties of soft tissues through which the particle beam passes.

In certain embodiments, the influence of a magnetic field produced by an MRI system on the particle beam and on the photon beam can also be taken into account in performing the real-time calculations of location of dose deposition. The patient MRI data and the radiation therapy beam information can be utilized to calculate accumulated dose deposition to the patient during the radiation therapy treatment. Optionally, the radiation therapy treatment can be re-optimized based on the calculated dose deposition.

Also disclosed is another computer program product that enables the receiving of patient radiation therapy prescription information and the receiving of patient magnetic resonance imaging (MRI) data. A radiation therapy treatment plan can be determined that includes combining photon beam delivery and particle beam delivery. The determining of the radiation therapy treatment plan can utilize the patient radiation therapy prescription information and the MRI data.

Implementations of the current subject matter can include, but are not limited to, methods consistent with the descriptions provided herein as well as articles that comprise a tangibly embodied machine-readable medium operable to cause one or more machines (e.g., computers, etc.) to result in operations implementing one or more of the described features. Similarly, computer systems are also contemplated that may include one or more processors and one or more memories coupled to the one or more processors. A memory, which can include a computer-readable storage medium, may include, encode, store, or the like, one or more programs that cause one or more processors to perform one or more of the operations described herein. Computer implemented methods consistent with one or more implementations of the current subject matter can be implemented by one or more data processors residing in a single computing system or across multiple computing systems. Such multiple computing systems can be connected and can exchange data and/or commands or other instructions or the like via one or more connections, including but not limited to a connection over a network (e.g., the internet, a wireless wide area network, a local area network, a wide area network, a wired network, or the like), via a direct connection between one or more of the multiple computing systems, etc.

The details of one or more variations of the subject matter described herein are set forth in the accompanying drawings and the description below. Other features and advantages of the subject matter described herein will be apparent from the description and drawings, and from the claims. While certain features of the currently disclosed subject matter are described for illustrative purposes in relation to particular implementations, it should be readily understood that such features are not intended to be limiting. The claims that follow this disclosure are intended to define the scope of the protected subject matter.

DESCRIPTION OF DRAWINGS

The accompanying drawings, which are incorporated in and constitute a part of this specification, show certain aspects of the subject matter disclosed herein and, together with the description, help explain some of the principles associated with the disclosed implementations. In the drawings.

DETAILED DESCRIPTION

Systems, methods and computer software are disclosed herein for the performance of radiotherapy that may utilize therapy provided by both photon beams (e.g., x-rays) and also by particle beams. Such may be utilized, as described herein, in combination with magnetic resonance imaging.

The disclosure below first introduces specific concepts relating to particle therapy, treatment planning for particle therapy, and particle therapy utilizing magnetic resonance imaging. Following such are descriptions of therapy that can combine particle therapy with photon beam therapy. It is contemplated and understood that the majority of concepts relating to particle therapy described our similarly applicable to the combination of particle therapy with photon beam therapy.

Particle therapy is a form of radiotherapy using beams of energetic particles for the treatment of disease, for example, cancer. Particle beams can be aimed at a target within a patient and can cause damage to the DNA and other important cellular components of the target cells, eventually causing the death of the cells. Cancerous cells have less ability than non-cancerous cells to repair radiation damage and are therefore particularly susceptible to particle therapy. Depending on the context, "particle therapy" is sometimes used to refer to therapy with hadrons, such as protons, neutrons, antiprotons, mesons, etc., while it may also refer to therapy utilizing ions or nuclei, such as lithium ions, helium ions, carbon ions, etc. Often, therapy with ions such as carbon ions is said to be "heavy ion therapy," although the line between "light ions" and "heavy ions" is not precisely defined. As used herein, the terms particle therapy, particle radiation therapy, particle beam and the like, refer to therapy utilizing hadrons as well as nuclei (or ions). This terminology specifically excludes therapies such as photon therapy or electron-beam therapy.

Figure 1:
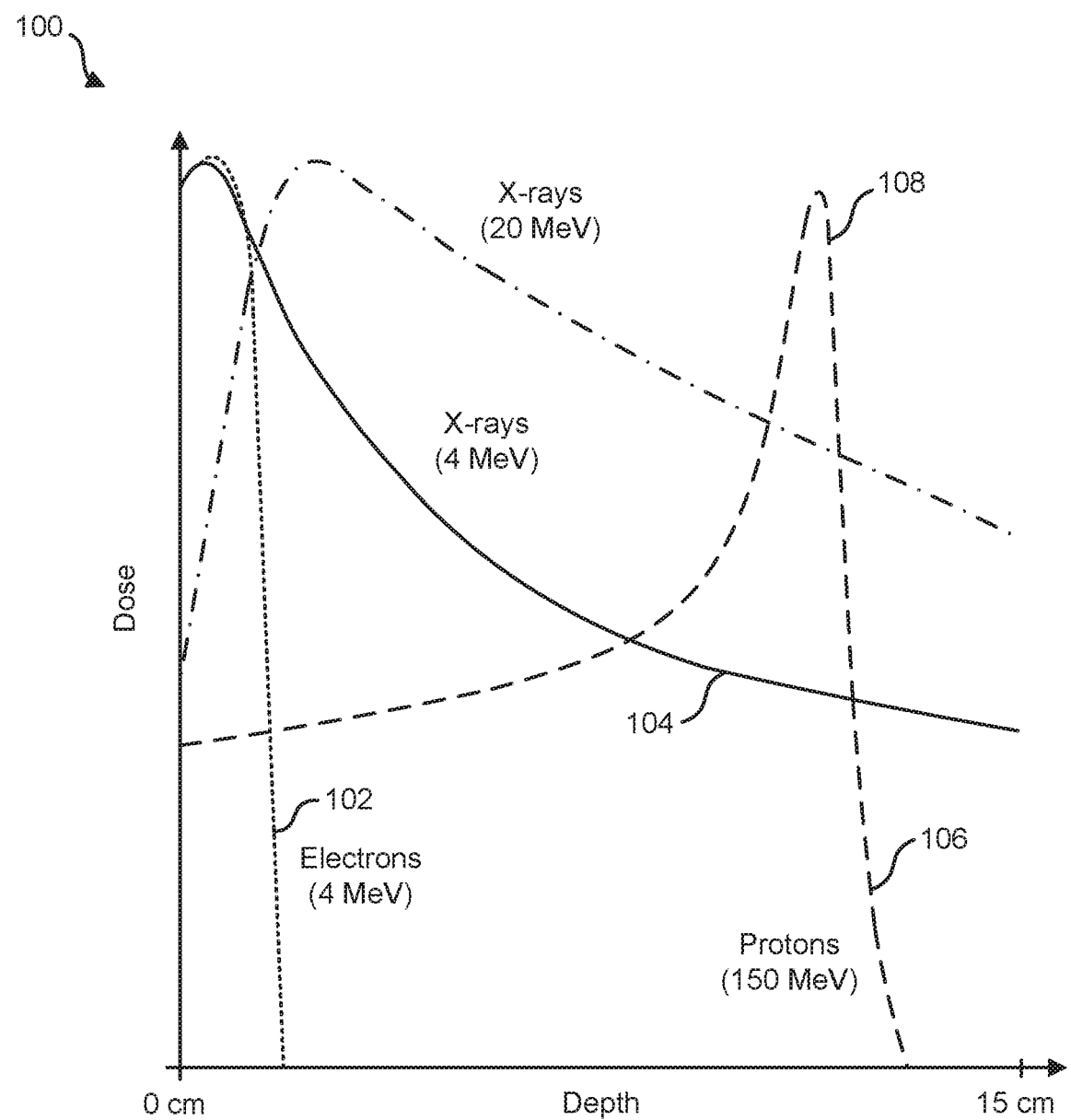
FIG. 1 is a graph showing the penetrative depth of various exemplary forms of radiation therapy into human tissue.

FIG. 1 is a graph 100 showing the penetrative depth of various forms of radiation therapy into human tissue. For a given energy, electron beams have a low penetrative depth into human tissue (as shown by trace 102) compared to other radiation therapy forms. X-ray beams penetrate human tissue to a greater depth than electrons, but the dose absorbed by tissue falls off with the penetrative depth of the X-rays as shown by trace 104. Particle therapy beams deposit more of their energy at a particular depth into the tissue of the patient at the end of their range, as shown by trace 108. This depth near the end of their range may be referred to as the Bragg Peak, shown as 108. A benefit provided by particle therapy is that less energy is deposited into healthy tissue outside of the target, thereby reducing the potential for damage to the healthy tissue. Additionally, beyond the Bragg peak there is very little dose deposited compared to X-Ray beams.

Before particle radiation therapy can take place, a treatment plan must be generated. The present disclosure contemplates the optional use of magnetic resonance imaging (MRI) data in a particular fashion in generating a treatment plan, which will have a predicted dose deposition closely matching the actual dose delivered to the patient and closely matching the desired dose. X-ray computed tomography (CT) imaging data may also be employed to determine, for example, the mass density of the patient's tissues and regions of the patient that contain low and high density tissues or regions such as lung, air, and bone. The analysis can be performed for all particle beam paths.

A magnetic resonance imaging system can be employed to obtain MRI data that, when analyzed, can more accurately determine the types of soft tissues along beam paths to and through the target. Particle interaction properties can then be determined from the MRI data, allowing for a more accurate determination of the dose delivered to the patient's tissues and to the target. In addition, the MRI data can enable more accurate determination of the biological effectiveness of the particle beam therapy.

The present disclosure contemplates that the MRI data may be combined with X-Ray CT data (for example, by using deformable image registration) to improve the accuracy of chemical composition and mass density determination and thus improve the determination of particle therapy doses. If X-Ray CT data is not available, regions containing bone may be determined by ultra-short echo time (TE) MR imaging, while lung and air may be determined from proton density weighted MR imaging.

X-Ray CT is well suited to produce a map of electron densities in the human body and is useful in determining dose delivered by photon beam radiation therapy because photons' dominant interaction probabilities are proportional to electron density. Electron densities are also well correlated to mass density due to the fact that, for human tissues, the atomic numbers are low where nuclei have a fairly constant ratio of neutrons to protons. CT Hounsfield numbers reflect the attenuation coefficient of human tissues to X-rays. Thus, the Hounsfield number may be identical for a variety of combinations of elemental compositions, elemental weights and mass densities, not to mention that the measured Hounsfield number may be inaccurate due to image beam hardening effects and other artifacts. The uncertainty of elemental composition introduced when defining tissues using X-Ray CTs and Hounsfield numbers can cause the determined range of a particle beam to err significantly. This error can lead directly to dose computation errors, for example, because particle stopping powers are required to accurately model dose deposition along an energetic particle's path and to determine where the particles reach the end of their range. Uncertainties in stopping power directly translate into uncertainties in the location of the Bragg peak 108, as illustrated in FIG. 1, which can move large dose regions off of targets and tumors, failing to deliver an effective dose to the treatment target and, instead, delivering particle radiation therapy dose to healthy tissues that should be shielded from receiving high doses of particle radiation.

Soft tissues have better contrast and definition when imaged with MRI systems over X-Ray CT. As noted, X-Ray CT is excellent at determining the mass density of tissues with very different densities and the definition of regions containing air or cortical bone, due to its low or high contrast and low or high Hounsfield numbers. But, many soft tissues will have very similar densities, with very different elemental compositions. For example, tissues can have a fat-like (or adipose-like) nature or a water-like (or muscle-like) nature while having a very similar mass density, and hence such are hard to distinguish with X-Ray CT data. Image noise, artifacts, and low contrast in X-Ray CT data conspire to often misidentify tissue types with current methods. In terms of stopping powers, removing any density dependence, the difference in stopping power between fat-like tissue (CH2) or water-like tissue (OH2) is dominated by the difference in atomic number between O and C. For energies above tens of MeV/nucleon, as used in particle therapy, the ratio of stopping powers is significant.

Acquiring MRI data with pulse sequences that are sensitive to only water or only fat, allows for the water-to-fat ratio of tissues to be determined through, for example, Dixon methods or sandwich echoes. The determined water-to-fat ratios in the vicinity of the treatment target can then be employed to improve the knowledge of the elemental compositions of the soft tissues. An MRI can obtain different "contrasts" by reading the signal of the excited protons at different times and/or in different ways (the signal decays differently depending on what type of molecule the hydrogen is attached to). It is therefore possible to better differentiate different tissue types and deduce chemical compositions utilizing an MRI.

The interactions (frequency and type of interaction) of a particle beam with the tissues it is passing through depends on a number of factors including beam particle type, particle energy, and the mass density and chemical composition of the tissue. Particle interactions, at least for charged particles, include Coulomb interactions (i.e., electromagnetic interactions). Coulomb interactions almost always lead to a small energy loss of the incident particle and/or a small deflection in direction. Deflections, which cause the beam to spread out, are referred to as Coulombic scattering. The amount of energy lost per unit length may be referred to as stopping power. The small energy losses that particles experience in Coulomb interactions are due to ionizations and excitations of the atoms and molecules of the tissue. The frequency of such interactions determines the ionization density along the path of a particle. The higher the ionization density, the higher the probability for cell damage. This is often measured with a quantity termed linear energy transfer (LET).

Particle interactions also include nuclear interactions, which are less frequent than Coulomb interactions but are much more catastrophic. They tend to result in the nucleus having been hit disintegrating into fragments (e.g., individual protons and neutrons, deuterons, tritons, lithiums, alphas, etc.). The type and number of such fragments depend on the incident particle type and energy, and the nucleus that has been hit. Nuclear interactions also leave behind radioactive nuclei, which decay and deposit additional dose.

Nuclear interactions and Coulombic scattering are highly dependent on atomic numbers of the nuclei. They both lead to broadening of a Bragg peak. For ions, nuclear interactions are also responsible for the tail of dose deposited beyond the Bragg peak. When there are heterogeneities in the beam path (e.g., air cavities, bones), Coulombic scattering leads to a complex dose deposition structure behind the heterogeneity.

When the term interaction properties is utilized herein, it refers to any combination of interaction properties such as the Coulombic interactions and nuclear interactions described above. Preferred embodiments of the present disclosure for, e.g., treatment planning or real-time MRI guidance of radiation therapy, will utilize as many interaction properties as necessary in determining the location and quantity of dose deposition in patient tissues.

"Heavy ions" such as Carbon ions tend to have a much more devastating effect on cells than protons. Their nuclear interaction fragments have high LETs and tend to deposit their energy locally around the interaction site. This is the main mechanism responsible for Carbon ions having a much higher "biological effectiveness" than protons. This leads to both more cells being killed (or damaged) per unit energy deposited in the tissue for ions compared to photons, electrons and even protons. The energy deposited in tissue is referred to as absorbed dose, measured in Gray (Gy). One Gy of absorbed dose from a Carbon ion beam will kill 3-12 times more cells than one Gy of absorbed dose from a photon or electron-beam, due to the differences in biological effectiveness.

With particle beam therapy, determination of the biological effectiveness is beneficial or even required for proper treatment. There are a number of different ways to determine biological effectiveness. For example, the determination of a biologically effective dose (BED) aims to indicate quantitatively the biological effect of a particular radiotherapy treatment, taking into account numerous factors such as the type of therapy, dose per fraction, dose rate, etc. In addition, relative biological effectiveness (RBE) is a ratio comparing the absorbed dose for a particular mode of therapy to an absorbed dose for photon therapy, where each dose leads to the same biological effect.

For protons, it has been assumed for years that RBE is constant at around 1.1, but some have opined that this leads to suboptimal planning results. Because the RBE for protons is so close to 1.0, neglecting to perform such a biological effectiveness calculation may not have too significant an effect on therapy but for neutrons, ions, mesons, etc., RBE is much higher and can have a very significant effect on therapy if not taken into account.

To determine biological effectiveness, one needs to know the energy spectrum of the incident beam as well as the interaction properties of the materials or tissues that the beam passes through. Thus, precise knowledge of the chemical composition of the tissues is absolutely essential for accurate determinations of biological effectiveness. It is also important to determine where the incident particle beam has lost the majority of its energy (i.e., the Bragg peak). In addition, contributions to the dose distribution due to nuclear reactions, activation of tissues, time dose fractionation and cell damage vs. recovery can be incorporated into determination of biological effectiveness. For these reasons, patient MRI data is important in the determination of biological effectiveness measures, similar to its importance in dose calculation and treatment planning.

MRI data can similarly be employed to allow evaluation of tissue elemental composition and accurate dose computation for the evaluation of the quality of a delivery plan before delivery. If the quality of the dose to be delivered is insufficient, the data collected at setup can be employed to re-optimize a particle therapy treatment plan before delivery. This can be performed immediately prior to delivery of the therapy, while the patient is on the treatment couch, or prior to the patient's arrival for the actual treatment.

Figure 2:
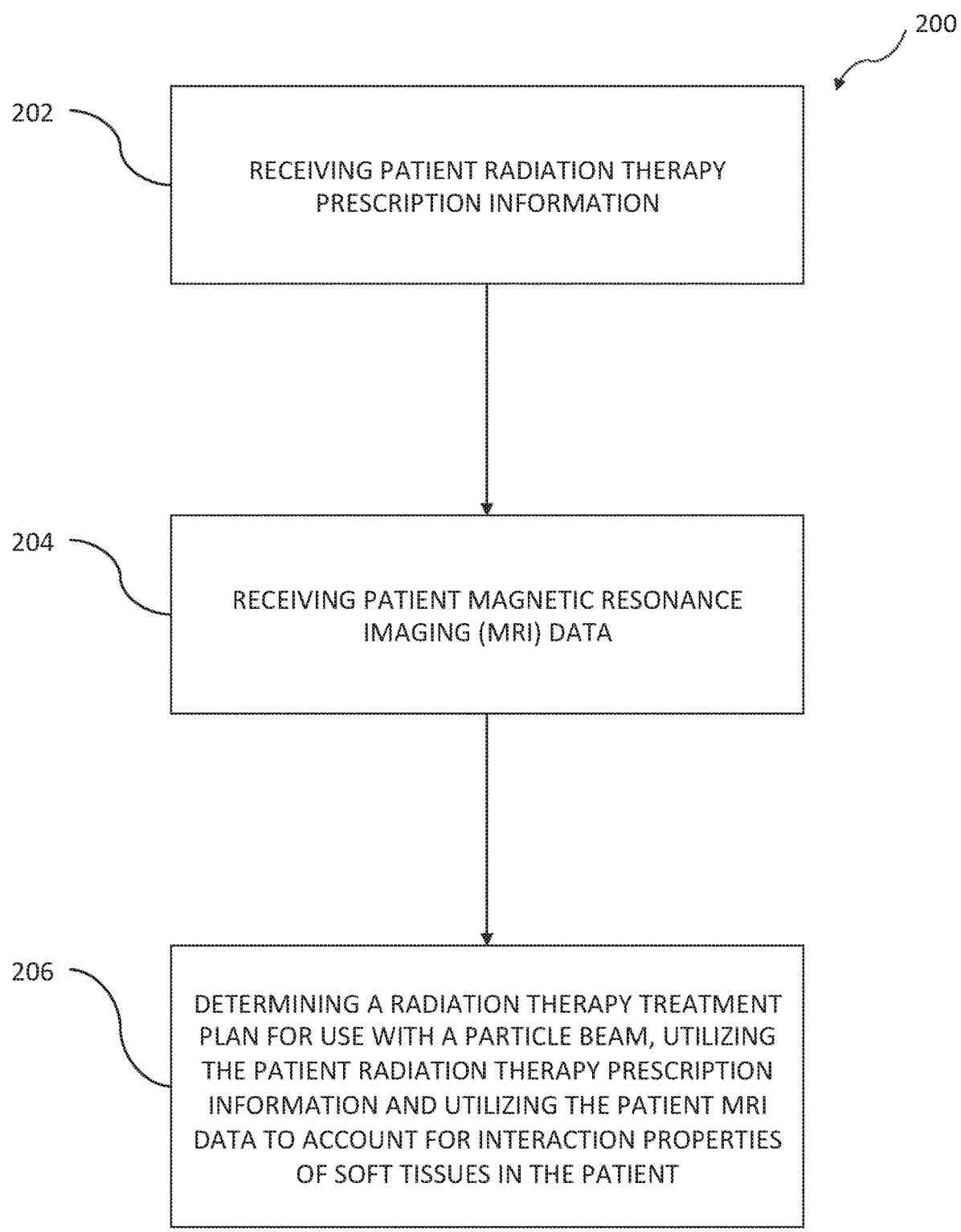
FIG. 2 is a flowchart for a method of radiation therapy treatment planning for particle radiation therapy, utilizing MRI data, that can be implemented by software.

FIG. 2 is a flowchart for a method 200 of radiation therapy treatment planning for particle radiation therapy, utilizing MRI data, that can be implemented by software, the method having one or more features consistent with the present description. The software can be implemented using one or more data processors that may be part of a system controller. The software can include machine-readable instructions, which, when executed by the one or more data processors, can cause the one or more data processors to perform one or more operations.

In FIG. 2, at 202, patient radiation therapy prescription information can be received. Patient radiation therapy prescription information may include data such as minimum dose required to a target tumor, maximum dose allowed to nearby organs of interest, or the like. The patient radiation therapy prescription information described herein is not intended to be limiting. The patient radiation therapy prescription information received at the radiation therapy treatment planning system can include prescription information typical for radiation therapy treatment planning.

At 204, patient MRI data can be received. In some variations, the patient MRI data can be received from a magnetic resonance imaging device integrated with a particle therapy system. Patient MRI data may encompass the region of interest for treatment, including, for example, a target treatment area of the patient and surrounding tissue that radiation therapy beams may pass through and for which radiation dose should be monitored. The MRI data may be taken before treatment at a different location from the treatment itself, or the MRI data may be acquired on the treatment table where an MRI is integrated with the particle radiation therapy system.

At 206, a radiation therapy treatment plan can be determined for use with a particle beam. The radiation therapy treatment plan can utilize the patient radiation therapy prescription information and utilize the patient MRI data to account for interaction properties of soft tissues in the patient through which the particle beam passes. The radiation therapy treatment plan can include, for example, the number of beams to be utilized, the direction from which the beam(s) will be delivered, the energy of the beam(s), collimator configurations, and the like.

Determination of the radiation therapy treatment plan can also account for the influence of the magnetic field of an MRI on the particle beam. This involves including the influence of the strong magnetic field of the MRI on transport of the ionizing radiation depositing dose in the patient. The interaction cross sections are not strongly influenced by polarization of spins as they compete with thermal effects (e.g., at body temperatures only about four parts per million of spins are aligned within a 1 Tesla magnetic field), but the magnetic field exerts an external Lorentz force on moving charged particles that can be accounted for to produce a more accurate dose computation.

Determination of the radiation therapy treatment plan can also include determination of a biological effectiveness of the dose delivered to the soft tissues of the patient by the particle beam, through utilization of the patient magnetic resonance imaging data.

Figure 3:
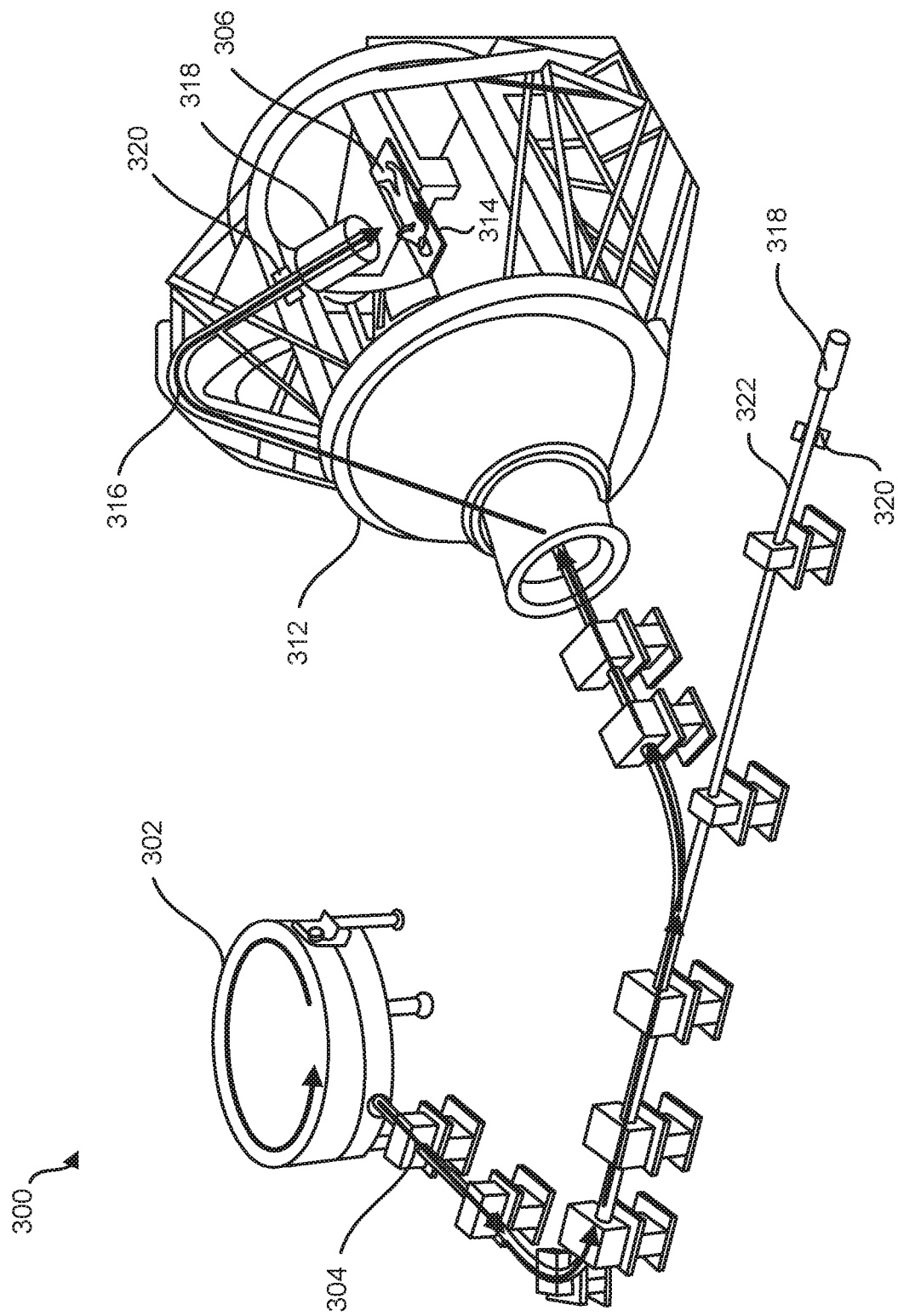
FIG. 3 is an illustration of a radiation therapy system having one or more features consistent with the present description.

FIG. 3 is an illustration of a particle therapy system 300 having one or more features consistent with the present description. To energize particles, the particles are first accelerated by a particle accelerator 302. The particle accelerator can be a synchrotron, cyclotron, linear accelerator, or the like. A synchrotron may be fed by either a low-energy cyclotron or a low-energy linear accelerator. The energy of the particle beam 304, prior to any downstream adjustment, determines the penetrative depth of the energized particles into the patient 306. Particle accelerators typically produce an energized particle beam having a defined energy. In some variations, the energy of the particles can be reduced, for example, by running the beam through an attenuating medium. It is preferable for such to be done away from the patient due to secondary neutrons that can increase unnecessary dose to the patient. The attenuating medium may be a wedge of material on a wheel or linear drive that can be rotated to increase or decrease the energy. The maximum energy is obtained by not applying any attenuating material in the beam. The minimum is obtained by applying the thickest amount of attenuating material in the beam. For a known material, a thickness can be determined that would halt all energized particles from reaching the patient to stop or interrupt the beam without deactivating the system.

Synchrotrons may also be configured to control beam energy by increasing or decreasing the number of passes through the accelerating elements in the synchrotron ring. In principle, a linear accelerator can also change the number of accelerating units, to a few fixed energies, over a limited range. Pulse to pulse energy changes are possible with the proper equipment.

In some variations, a particle therapy gantry 312 can be used to direct the energized particle beam 304 to the patient 306. The patient 306 can be positioned on a couch 314 within the center of the particle therapy gantry 312. The particle therapy gantry 312 can include gantry electromagnets 316 configured to direct the beam toward the patient 306, through a dosimetry system 318.

The particle therapy gantry 312 can be configured to rotate to facilitate delivery of particle therapy at different angles. In some variations, the particle therapy gantry 312 can be configured to rotate 360 degrees. One or more slip rings can be employed to facilitate the delivery of electrical power to the electro-magnets other components disposed on the particle therapy gantry 312. In some variations, the particle therapy gantry 312 can be configured to rotate with a field of rotation of approximately 360 degrees. In such variations, the particle therapy gantry 312 may rotate in one direction as far as it will go and then rotate back in the other direction as far as it will go. Rotating the particle therapy gantry 312 around the patient 306 can facilitate delivery of the energized particle beam 304 to the target at different angles improving the sparing of healthy tissue and treatment plan quality.

The particle therapy gantry 312 may include scanning beam magnets 320. The scanning beam magnets 320 can include, for example, pairs of electro-magnets. The pairs of electro-magnets can be arranged to have their magnetic fields in orthogonal planes to one another. The scanning beam magnets 320 can be configured to manipulate the direction of the energized particle beam 304. In some variations, scanning beam magnets 320 can be configured to direct the energized particle beam in a scanning motion back and forth across the treatment target of the patient.

In some variations, the system can include a fixed beamline 322. The fixed beamline 322 can be configured to deliver the energized particles directly to a patient through a dosimetry system 318, without a gantry. The system may also include one or more scanning beam electro-magnets 320 configured to modify the direction of the energized particles of the fixed-line beam.

The particle therapy system may also include a scatterer. The scatterer can be configured to cause the energized particle beam 304 to scatter outward. The system can also contain a beam wobbler or raster scanning mechanism to spread out the beam. The system can also include a collimator. The collimator can be a multi-leaf collimator comprising a plurality of thin metallic blades. The thin metallic blades can be moveable, the position of which can be controlled by a computer. The thin metallic blades can be configured to absorb the energetic particles. The thin metallic blades can be arranged, by a controller, such that the shape of an aperture they form is complementary to the target within the patient. In this manner, the collimator can facilitate shielding of healthy tissue surrounding the target while permitting the energized particles to penetrate to the target. In some variations, a collimator carved into a permanent shape may be used. Similarly, a bolus can be positioned in the path of the energized particle beam 304, which may be formed from a material semi-permeable to the energized particles, and may be carved to compliment the shape of the tumor.

Figure 4:
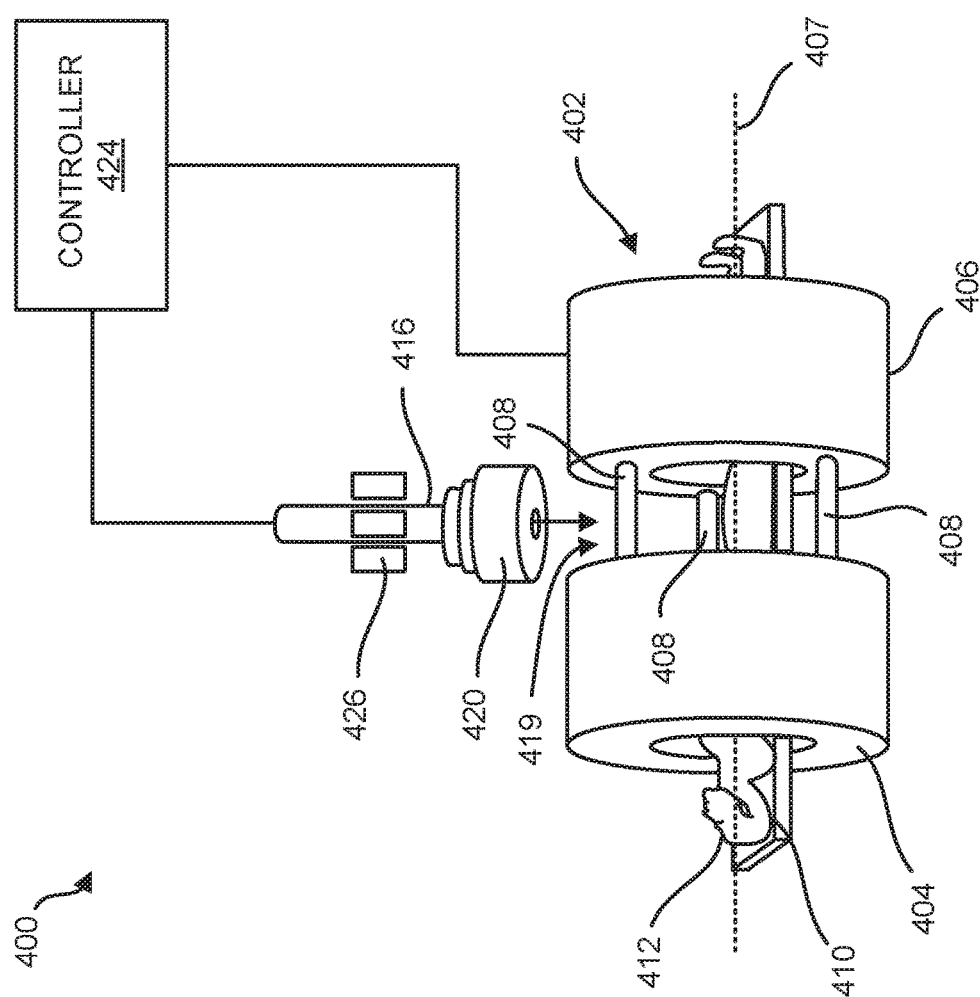
FIG. 4 is an illustration of a radiation therapy system having one or more features consistent with the present description.

FIG. 4 is an illustration of a particle therapy delivery system 400 having one or more features consistent with the present disclosure. The particle therapy delivery system 400 can have one or more elements similar to the elements of the system 300, illustrated in FIG. 3. The particle therapy system 400, according to the present disclosure, may include a particle therapy delivery system for delivery of radiation therapy to a patient via a particle beam, a magnetic resonance imaging system 402 configured to obtain patient magnetic resonance imaging (MRI) data during radiation therapy; and, a controller 424 configured to receive patient MRI data during radiation therapy and utilize the patient MRI data to perform real-time calculations of the location of dose deposition for the particle beam(s), taking into account interaction properties of the soft tissues in the patient through which the particle beam passes.

The particle therapy delivery system 400 may include a split magnet MRI 402. The split magnet MRI 402 can include two split main magnets 404 and 406. The radiation therapy system can include an isocenter 407. The two split main magnets 404 and 406 can be separated by a plurality of buttresses 408. The plurality of buttresses 408 can be located no further from the isocenter 407 than the outer boundary of the two split main magnets 404 and 406. While the two split main magnets 404 and 406 are each referred to as a single magnet, this terminology is not intended to be limiting. The two split main magnets 404 and 406 can each include a plurality of magnets for the purpose of obtaining MRI data of the patient.

A split MRI system is illustrated in FIG. 4 for illustrative purposes only. The MRI system used can be any type of MRI system. For example, the main magnets can include vertical open magnets, short bore magnets, magnets with a portal or thin section, or the like.

A couch 410 can be disposed within the split MRI system 402. The split MRI system 402 can be configured to receive a patient 412, on the couch 410, through the internal apertures of the two split main magnets 404 and 406.

The split magnet MRI system 402, couch 410 and patient 412 can all be disposed within a particle therapy gantry, such as gantry 312 illustrated in FIG. 3. The particle therapy gantry may be configured to rotate about the patient 412 delivering particle therapy to the patient from a multitude of angles.

The plurality of buttresses 408 can be disposed between the two main MRI magnets 404 and 406 and positioned within the outer periphery of the two main MRI magnets 404 and 406 so as not to further increase the overall diameter of the MRI system. The system may include, as an example, three buttresses 408 spaced at equal angles around the two main MRI magnets 404 and 406. The system can be operated such that the particle beam is directed toward the patient between the split magnets and in a manner such that it will not travel through any of the buttresses 408.

The particle therapy system can be configured to facilitate delivery of energized particles to the patient such that the energized particles are directed into a gap 419 between the two main MRI magnets 404 and 406.

Particle therapy delivery system 400 can include a dosimetry system 416 for monitoring the radiation therapy to the patient. The dosimetry system 416 can also include one or more components to facilitate the delivery of particle therapy to the patient, for example, by providing feedback to a controller.

The particle therapy delivery system 400 can include one or more shielding structures 420 that may, for example, surround at least a portion of the dosimetry system. Shielding structures 420 can be configured to house electronic equipment that would otherwise be adversely affected by radiofrequency interference or by the magnetic fields produced by main MRI magnets 404 and 406.

Figure 5A:
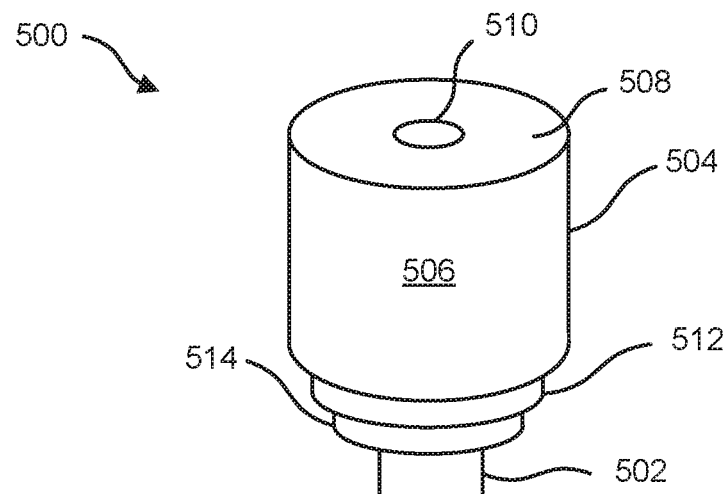
FIGS. 5A-5B illustrate a shielding system for shielding, for example, a portion of a dosimetry system of a particle therapy system, having one or more features consistent with the current description.
Figure 5B:
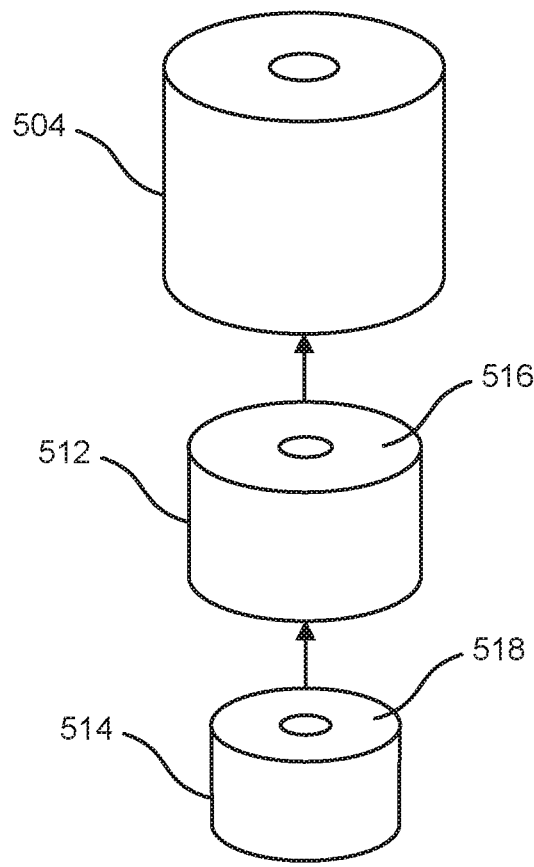

FIGS. 5A-5B illustrate an exemplary shielding structure 500 for shielding at least a portion of a dosimetry system 502 of a particle therapy delivery system, having one or more features consistent with the present disclosure. The shielding structure 500 may comprise a plurality of shells. The plurality of shells can be formed from a series of concentric shields configured to shield magnetic fields produced by the split magnet MRI system 402 illustrated in FIG. 4. The concentric shields may be configured to surround at least a portion of a dosimetry system 502. The present disclosure further contemplates shielding structures that may include one or more layers of RF absorbing materials or RF reflecting materials, or combinations of both to, for example, minimize potentially adverse effects of RF radiation emanating from a linear accelerator utilized in certain aspects of the disclosure.

The shielding structure 500 can include a first shield container 504. The first shield container 504 can comprise a cylindrical body portion 506 and an annular disk 508 disposed across one end of the cylindrical body portion. The annular disk 508 can include an aperture 510 to allow the particle particles to pass through unhindered. In some variations, the first shield container 504 can have a diameter of approximately seventeen inches. The diameter of the first shield container 504 can be selected to sufficiently house at least a portion of the components of the dosimetry system 502.

The shielding structure 500 can comprise a plurality of shells. For example 504, 512 and 514 in FIG. 5B, or the like. The plurality of shells 504, 512, 514 can be nested together. At least one of the plurality of shells preferably includes an annular disk 516, 518, or the like.

The shielding structure 500 may be positioned in a fixed location with respect to split magnet MRI system 402, or may be configured to rotate with a gantry, such as gantry 312 illustrated in FIG. 3. One or more structures can be disposed opposite or around the split magnet MRI system 402 and configured to mimic the magnetic properties of shielding structure 500 in order to minimize interference with the homogeneity of the MRI's magnetic fields.

Figure 6:
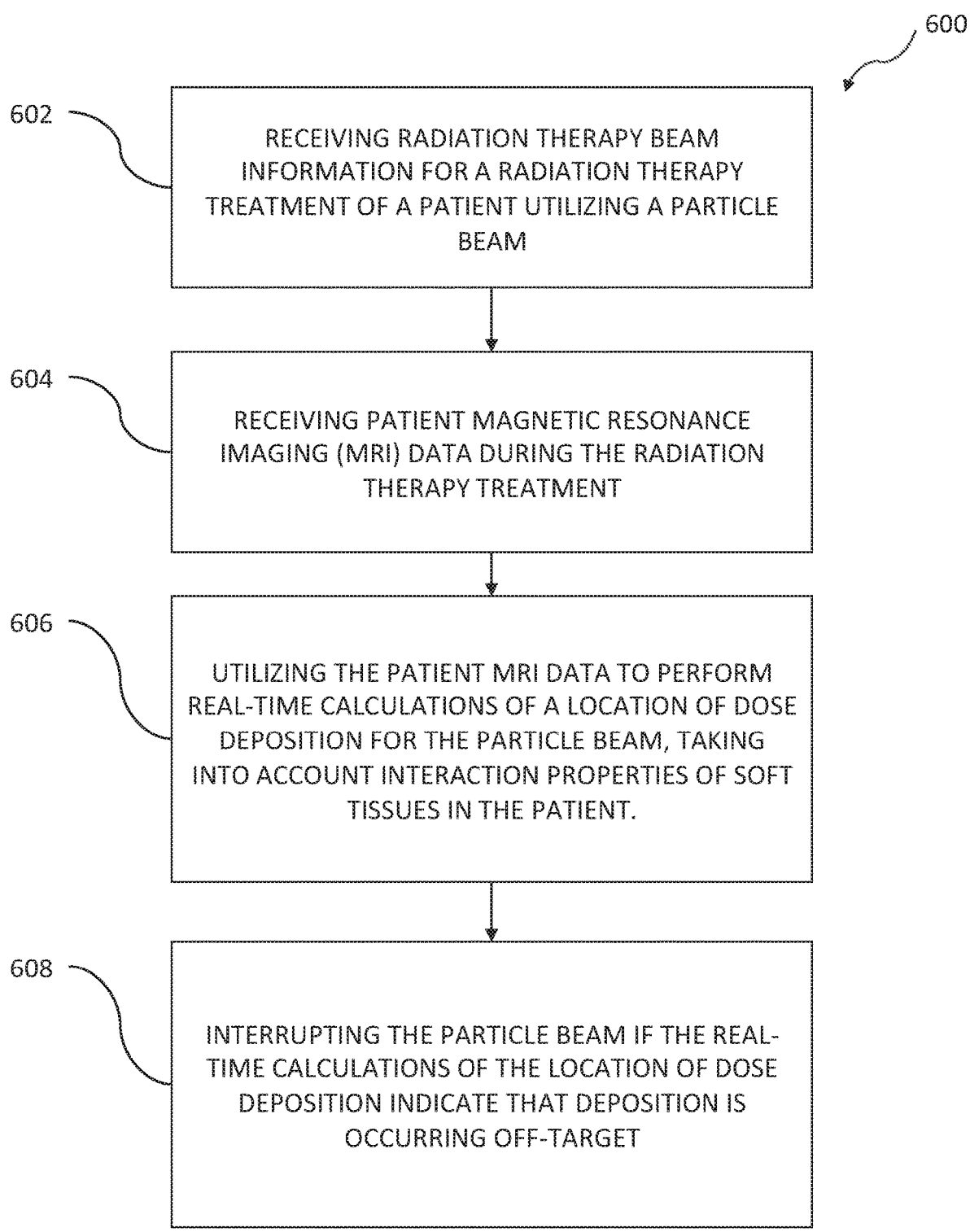
FIG. 6 is a flowchart for a method of particle radiation therapy treatment having one or more elements consistent with the present description.

FIG. 6 is a flowchart for a method 600 of radiation therapy treatment for particle radiation therapy, utilizing MRI data, that may be implemented by software, the method having one or more features consistent with the present description. The software can be implemented using one or more data processors. The software can include machine-readable instructions, which, when executed by the one or more data processors, can cause the one or more data processors to perform one or more operations. Method 600 is an example of the operations that can be performed by controller 424, as discussed herein.

At 602, radiation therapy beam information for radiation therapy treatment of a patient utilizing a particle beam can be received. The radiation therapy beam information can include one or more characteristics of a particle beam. The one or more characteristics can include an indication of penetrative abilities of the particle beam, the spread characteristics of the particle beam, the number of particle beams, or the like.

At 604, patient magnetic resonance imaging (MRI) data can be received during the radiation therapy treatment.

At 606, the patient MRI data can be utilized to perform real-time calculations of a location of dose deposition for the particle beam, taking into account interaction properties of soft tissues in the patient through which the particle beam passes, as discussed herein. The influence of a magnetic field produced by an MRI system on the particle beam may also be accounted for in performing the real-time calculations of location of dose deposition, as discussed above. And, a determination of the biological effectiveness of dose delivered to the soft tissues by the particle beam, through utilization of the patient magnetic resonance imaging data, may also be performed in conjunction with the real-time dose calculations.

At 608, the particle beam can be interrupted if real-time calculations of the location of dose deposition indicate that deposition is occurring off-target.

In some variations, the energy of the particle beam can be adjusted if the real-time calculations of the location of dose deposition indicate that deposition is occurring off-target. In other variations, the patient MRI data can be utilized and the real-time calculations of the location of dose deposition to modify a direction of the particle beam in order to track a target.

As further detailed herein, concepts described with regard to the exemplary method for radiation therapy of FIG. 6 may also be utilized in systems, methods and computer software combining particle therapy with photon therapy.

In certain implementations of the present disclosure, a particle therapy delivery system may be combined with a photon therapy delivery system and the system controller can be configured to facilitate the delivery of both particle beams and photon beams. For example, particle therapy (such as proton therapy) may be delivered in combination with therapy from a linear accelerator configured to deliver an x-ray beam. The combined system may be configured such that the particle therapy and photon therapy are delivered alternatively during a treatment session, but without requiring movement of the patient between therapy types. The patient is preferably located on a couch with respect to an isocenter shared by both the particle therapy system and the photon therapy system (although small patient movements are contemplated within the spirit of the disclosure).

In a combined particle/photon therapy system, the particle therapy system may be configured to have a single fixed beam line, multiple fixed beam lines, or a gantry system, and the photon therapy system may be configured to deliver photon beams from a multitude of angles (e.g., via a rotating gantry, a robotic arm, or the like).

Preferred embodiments of the present disclosure do away with the need for a particle therapy gantry system, instead delivering particle therapy from one or a small number of fixed beam lines and supplementing such therapy with photon beam therapy that can be delivered from a greater number of angles. Such combined therapy systems can result in higher quality treatment plans that, for example, can improve the sparing of healthy tissue surrounding a treatment target.

Figure 7:
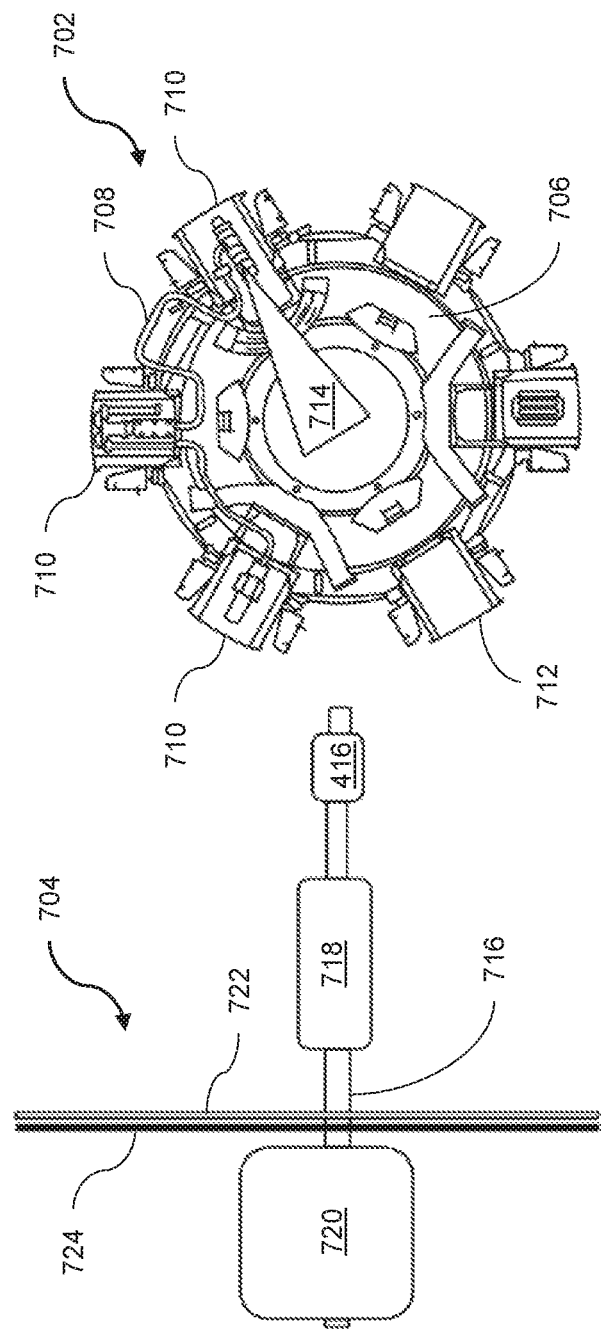
FIG. 7 is an illustration of a combined radiation therapy system having one or more features consistent with the present description.

FIG. 7 illustrates an exemplary radiation therapy system combining aspects of a photon therapy delivery system 702 and a particle therapy delivery system 704 (only portions of which are depicted in the figure). Photon therapy system 702 in the FIG. 7 example is a linear accelerator configured to produce x-ray beams, however, the present disclosure contemplates alternative photon therapy systems including radioisotopes, etc. Electron-beam systems may also be utilized.

FIG. 7 depicts one particular implementation of photon therapy delivery system 702 where portions of a linear accelerator are disposed around a gantry 706. Such portions may be separated to different positions on gantry 706 and may be connected to one another utilizing RF waveguides 708. The present disclosure further contemplates that one or more portions of the photon therapy system may be contained within shielding structures 710 that may take forms similar to the shielding structures discussed above with regard to FIG. 5.

Gantry 706 may also include an additional empty shielding structure 712 configured to shield at least a portion of the dosimetry system 416 of the particle therapy system 704. Such an empty shielding structure 712 can similarly take the form of any of the shielding structures discussed above with regard to FIG. 5. Although the embodiment depicted in FIG. 7 shows an empty shielding structure 712 mounted on the gantry, is also contemplated that the particle therapy dosimetry system's shielding structure may be mounted independent of the gantry, for example, mounted directly to the floor, adjacent photon therapy system 702 and its gantry 706.

Figure 8:
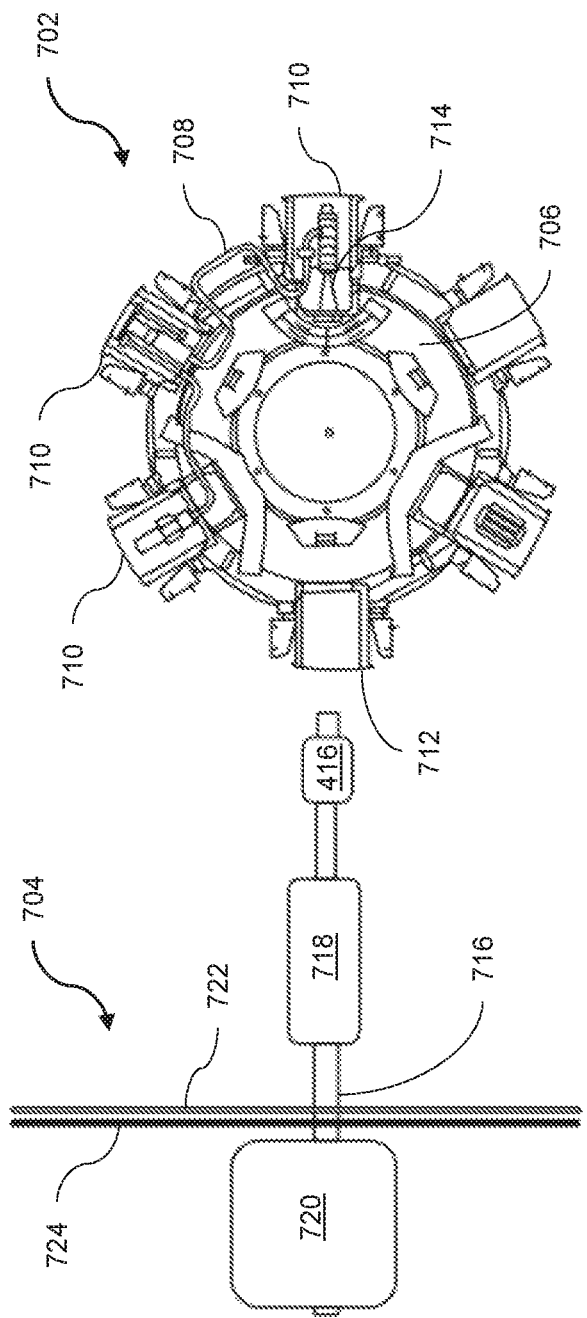
FIG. 8 is an illustration of a combined radiation therapy system having one or more features consistent with the present description.
Figure 9:
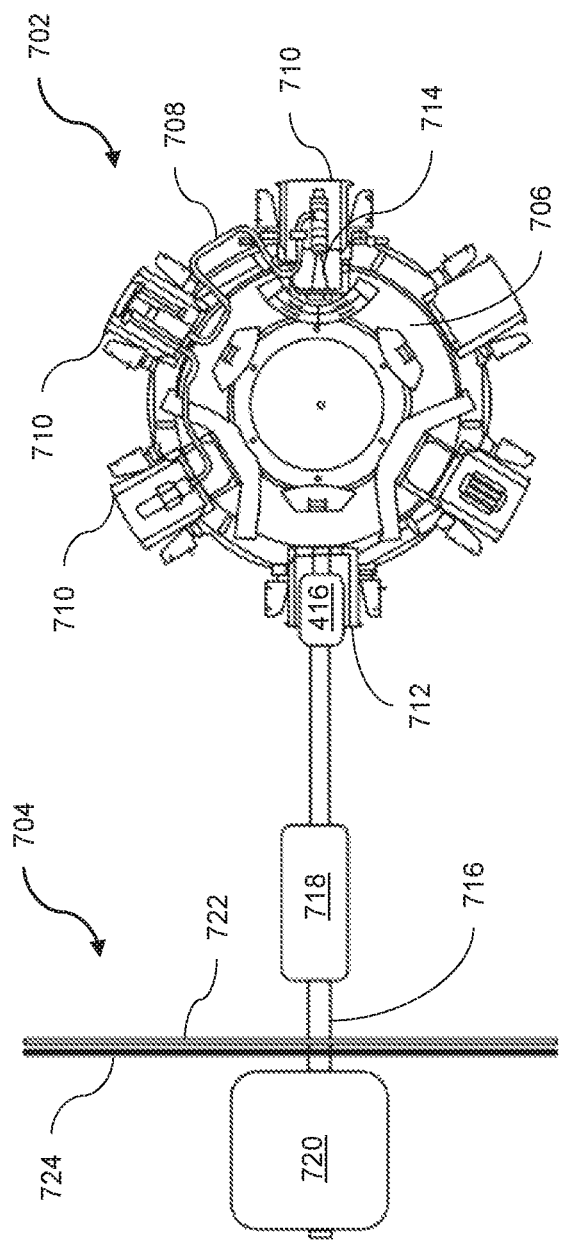
FIG. 9 is an illustration of a combined radiation therapy system having one or more features consistent with the present description.

In operation, photon therapy delivery system 702 is configured to deliver a photon beam 714 from various angles toward a patient, and the combined radiation system can be utilized to deliver particle therapy in the exemplary manner partially depicted in FIGS. 8 and 9. In this exemplary manner of operation, gantry 706 can be rotated so that empty shielding structure 712 is aligned with a particle therapy beam line 716, as shown in FIG. 8. Following such, a beam line extender 718 can be utilized to extend the particle therapy system's dosimetry system 416 to a location at least partially within empty shielding structure 712, as depicted in FIG. 9. A telescoping vacuum chamber is one example of a beam line extender although other methods for changing the position of the particle therapy system's dosimetry elements are contemplated.

As noted above, the present disclosure also contemplates embodiments where the particle dosimetry system's shielding structures are located off of the gantry. In such embodiments, a beam line extender may not be required. In addition, an empty shielding structure may not be required on gantry 706 and instead gantry 706 may simply be rotated to a position that will ensure minimal interference with the particle therapy beam by the photon therapy system equipment.

In some implementations of the present disclosure, certain particle therapy delivery system components may be beneficially located away from the photon therapy delivery system. In one example, particle therapy system deflection/bending magnets may be located away from the photon therapy system or even outside of the patient therapy vault. Fringe shielding may be employed to isolate such components 720 from photon therapy delivery system 702 and may include, for example, RF shielding 722 and/or magnetic shielding 724. Such fringe shielding may also be employed to isolate such components 720 from a magnetic resonance imaging system that may be utilized with the combined photon/particle therapy system.

The combined photon and particle therapy systems of the present disclosure may be utilized with a magnetic resonance imaging system, as previously described above with regard to particle therapy. For example, the magnetic resonance imaging system 402 depicted in FIG. 4 may be employed in conjunction with a combined particle/photon system, an example of which is depicted in FIG. 7. In such an example, the photon therapy system 702 and its gantry 706 may be disposed within the gap 419 of FIG. 4's magnetic resonance imaging system 402.

As discussed above with respect to particle therapy, integration of magnetic resonance imaging with a combined particle/photon therapy system similarly results in the realization of a number of benefits. This disclosure contemplates each of the applicable benefits discussed above being realized with the combined particle/photon system including, but not limited to, the ability of the system to receive patient magnetic resonance imaging (MRI) data during treatment and to utilize such data to perform real-time calculations of the location of dose deposition for a particle beam and also for a photon beam. In addition, the system's controller can be configured to interrupt the particle beam and/or the photon beam if the real-time calculations of the location of dose deposition indicate that dose deposition is occurring off-target. Also, the system may be configured to calculate accumulated dose deposition to the patient during a radiation therapy treatment and to re-optimize treatment based on the calculated dose deposition.

The present disclosure contemplates that the calculations disclosed in the embodiments herein may be performed in a number of ways, applying the same concepts taught herein, and that such calculations are equivalent to the embodiments disclosed.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers. A client and server are generally remote from each other and typically interact through a communication network. The relationship of client and server arises by virtue of computer programs running on the respective computers and having a client-server relationship to each other.

These computer programs, which can also be referred to programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" (or "computer readable medium") refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" (or "computer readable signal") refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on," above and in the claims is intended to mean, "based at least in part on," such that an unrecited feature or element is also permissible.

The subject matter described herein can be embodied in systems, apparatus, methods, computer programs and/or articles depending on the desired configuration. Any methods or the logic flows depicted in the accompanying figures and/or described herein do not necessarily require the particular order shown, or sequential order, to achieve desirable results. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. The implementations described above can be directed to various combinations and subcombinations of the disclosed features and/or combinations and subcombinations of further features noted above. Furthermore, above described advantages are not intended to limit the application of any issued claims to processes and structures accomplishing any or all of the advantages.

Additionally, section headings shall not limit or characterize the invention(s) set out in any claims that may issue from this disclosure. Further, the description of a technology in the "Background" is not to be construed as an admission that technology is prior art to any invention(s) in this disclosure. Neither is the "Summary" to be considered as a characterization of the invention(s) set forth in issued claims. Furthermore, any reference to this disclosure in general or use of the word "invention" in the singular is not intended to imply any limitation on the scope of the claims set forth below. Multiple inventions may be set forth according to the limitations of the multiple claims issuing from this disclosure, and such claims accordingly define the invention(s), and their equivalents, that are protected thereby.

What is claimed is:

1. A radiation therapy system comprising:
   a photon therapy delivery system for delivery of radiation therapy to a patient via a photon beam, the photon therapy delivery system is at least partially mounted on a gantry and having at least a portion of the photon therapy delivery system contained within a shielding structure, the photon therapy delivery system configured to deliver radiation therapy to a patient via photon beams from multiple directions;
   a second shielding structure mounted on the gantry and configured to shield at least a portion of a particle therapy dosimetry system; and
   a controller configured to facilitate delivery of radiation therapy via a photon beam and also a particle beam.

2. The radiation therapy system of claim 1 wherein the delivery of radiation therapy via a photon beam and the delivery of radiation therapy via a particle beam can both be completed without having to move the patient.

3. The radiation therapy system of claim 1 wherein the photon therapy delivery system is a linear accelerator and the photon beam is an x-ray beam.

4. The radiation therapy system of claim 1, further comprising a beamline extender configured to facilitate repositioning of a particle therapy dosimetry system for the delivery of therapy from a position at least partially within the second shielding structure configured to shield at least a portion of the particle therapy dosimetry system.

5. The radiation therapy system of claim 4, further comprising a particle therapy delivery system.

6. The radiation therapy system of claim 5, wherein the particle therapy delivery system is a proton therapy system and the particle beam is a proton beam.

7. The radiation therapy system of claim 5, further comprising fringe field shielding.

8. The radiation therapy system of claim 1, further comprising:
   a magnetic resonance imaging system (MRI) configured to acquire images of the patient during administration of radiation therapy.

9. A non-transitory computer program product storing instructions that, when executed by at least one programmable processor forming part of at least one computing system, cause the at least one programmable processor to perform operations comprising:
   receiving radiation therapy beam information for a radiation therapy treatment of a patient utilizing a particle beam and a photon beam;
   receiving patient magnetic resonance imaging (MRI) data during the radiation therapy treatment; and
   utilizing the patient MRI data to perform real-time calculations of a location of dose deposition for the particle beam and for the photon beam, taking into account interaction properties of soft tissues through which the particle beam passes.

10. The computer program product of claim 9 further comprising taking into account influence of a magnetic field produced by an MRI system on the particle beam and on the photon beam in performing the real-time calculations of location of dose deposition.

11. The computer program product of claim 9 further comprising:
    interrupting the particle beam or the photon beam if the real-time calculations of the location of dose deposition indicate that dose deposition is occurring off-target.

12. The computer program product of claim 9 further comprising:
    utilizing the patient MRI data and the radiation therapy beam information to calculate accumulated dose deposition to the patient during the radiation therapy treatment.

13. The computer program product of claim 12 further comprising:
    re-optimizing the radiation therapy treatment based on the calculated dose deposition.

14. The computer program product of claim 9 further comprising:
    causing a controller to reposition a particle therapy dosimetry system.

15. The computer program product of claim 14, wherein the controller repositions the particle therapy dosimetry system by operating a beam line extender.

16. The computer program product of claim 14, wherein the controller repositions the particle therapy dosimetry system to a position at least partially within a shielding structure mounted on a gantry.

* * * * *